(12) United States Patent
Masuda et al.

(10) Patent No.: US 7,522,709 B2
(45) Date of Patent: Apr. 21, 2009

(54) X-RAY EXAMINATION APPARATUS AND X-RAY EXAMINATION METHOD USING THE SAME

(75) Inventors: Masayuki Masuda, Nishinomiya (JP); Tsuyoshi Matsunami, Kyotanabe (JP); Haruyuki Koizumi, Kyoto (JP)

(73) Assignee: Omron Corporation, Kyoto-Shi (JP)

( * ) Notice: Subject to any disclaimer, the term of this patent is extended or adjusted under 35 U.S.C. 154(b) by 0 days.

(21) Appl. No.: 12/048,852

(22) Filed: Mar. 14, 2008

(65) Prior Publication Data
US 2008/0226035 A1  Sep. 18, 2008

(30) Foreign Application Priority Data
Mar. 15, 2007  (JP) ............................. P2007-067043

(51) Int. Cl.
*G21K 1/00* (2006.01)
(52) U.S. Cl. ........................... 378/145; 378/124; 378/62
(58) Field of Classification Search ................... 378/62, 378/96, 97, 108, 119, 124, 137, 138, 143, 378/144, 145, 146
See application file for complete search history.

(56) References Cited

U.S. PATENT DOCUMENTS

2005/0063514 A1 * 3/2005  Price et al. .................. 378/119

FOREIGN PATENT DOCUMENTS

JP    2000-46760    2/2000

* cited by examiner

*Primary Examiner*—Courtney Thomas
(74) *Attorney, Agent, or Firm*—Foley & Lardner LLP

(57) ABSTRACT

An X-ray examination apparatus changes a position of each X-ray sensor by rotating a sensor base, and resets a starting position of X-ray emission that becomes a X-ray focal position so that the X-ray enters each X-ray sensor after the position thereof is changed. A scanning X-ray source deflects an electron beam to easily change the position where the electron beam impinges a target of the X-ray source to an arbitrary location. The irradiating position of the electron beam then can be easily moved according to an accumulated irradiation time on the target. Therefore, maintenance can be performed without interrupting the X-ray examination.

12 Claims, 14 Drawing Sheets

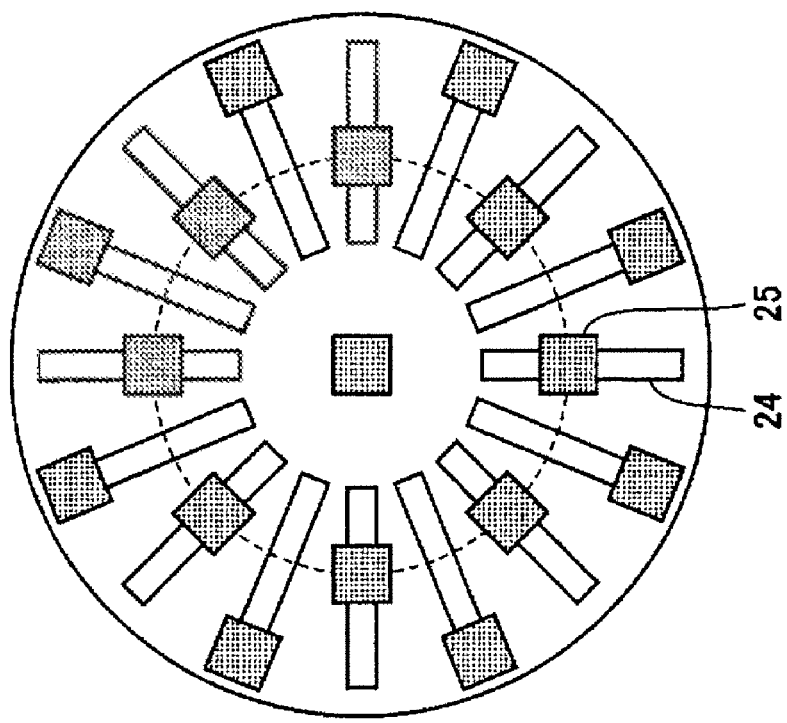
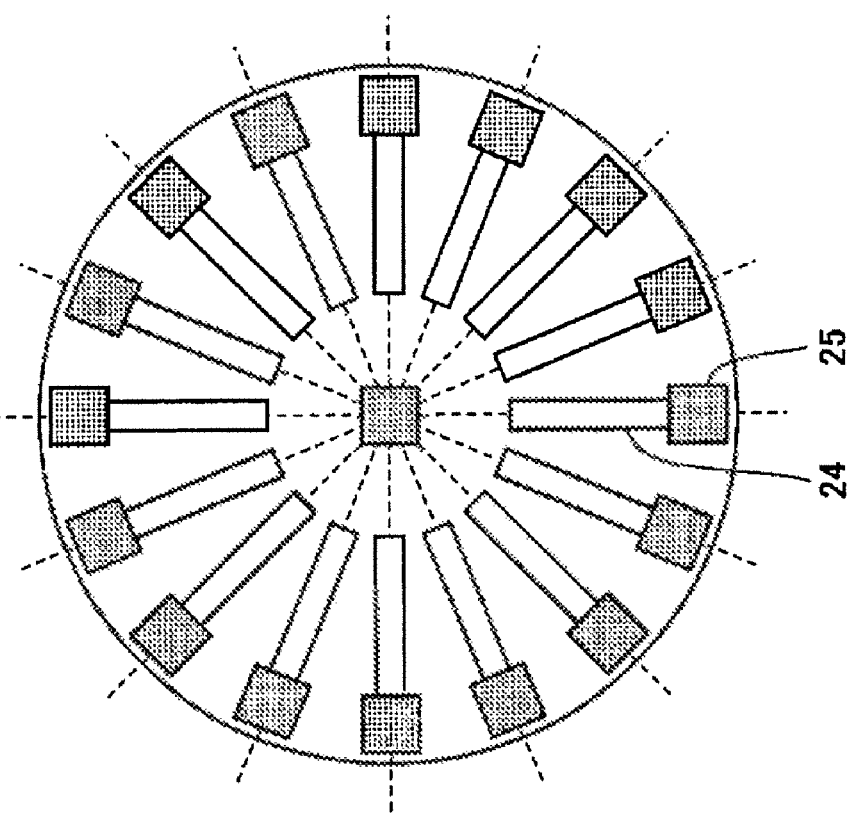

Sensor base reference angle = 0 degree

Sensor base reference angle = θs

Sensor base reference angle = θs
Target maintenance angle = θ m

Sensor base reference angle = 0 degree
Target maintenance angle = θ m

Target Surface

Fig. 9

Currently used target maintenance information  200

| X-ray focal position (202) | Accumulated X-ray irradiation time (204) |
|---|---|
| P1 | T1 |
| P2 | T2 |
| ... | ... |
| Pn | Tn |

Fig. 10

Previously used target maintenance information  210

| X-ray focal position (212) | Accumulated X-ray irradiation time (214) |
|---|---|
| M1 | Tm1 |
| M2 | Tm2 |
| ... | ... |
| Mn | Tmn |
| ... | ... |
| Mx | Tmx |
| ... | ... |

Fig. 11

NG target maintenance information  220

| X-ray focal position (222) | Accumulated X-ray irradiation time (224) | Automatic determination flag (226) |
|---|---|---|
| N1 | Tn1 | ON |
| N2 | Tn2 | ON |
| ... | ... | ... |
| Nn | Tnn | OFF |

X-RAY EXAMINATION APPARATUS AND X-RAY EXAMINATION METHOD USING THE SAME

This application claims priority from Japanese Patent Application P2007-067043, filed on Mar. 15, 2007. The entire content of the aforementioned application is incorporated herein by reference.

BACKGROUND OF THE INVENTION

1. Field of the Invention

The present invention relates to an X-ray examination apparatus and an X-ray examination method using the same.

2. Description of the Related Art

Recently, with high integration of an LSI (Large-Scale Integration) by submicron microfabrication technique, functions which were divided into a plurality of packages in the prior art can now be integrated into one LSI. Since increase in the number of pins that arise as a result of incorporating the functions necessary for one package cannot be responded with the conventional QFP (Quad Flat Package) and PGA (Pin Grid Array), LSI of BGA (Ball Grid Array) and CSP (Chip Size Package) package, in particular, is recently being used. The BGA package is used where ultraminiaturization is necessary such as a portable telephone even if the required number of pins is not great.

The BGA and CSP package of the LSI greatly contribute to ultraminiaturization, but has a feature in that the solder portion etc. cannot be seen from the outer appearance after assembly. When inspecting a print substrate etc. mounted with the BGA or CSP package, the quality determination is performed by analyzing a transmissive image obtained by irradiating an X-ray onto an examining object. For instance, patent document 1 (refer to, for example, Japanese Patent Application Laid-Open Publication No. 2000-46760) discloses an X-ray sectional examination apparatus capable of obtaining a clear X-ray image by using an X-ray planar sensor to detect the transmissive X-ray.

In such an X-ray examination apparatus, the X-ray is emitted by impinging the electron beam onto a target such as tungsten. When the electron beam impinges the target, the target is damaged. Thus, the target deteriorates if the electron beam is impinged on the same position of the target for greater than or equal to a predetermined time.

The X-ray source of the X-ray examination apparatus includes a method in which a position of impinging the electron beam onto the target is fixed (fixed focus method), and a method in which the electron beam is repeatedly impinged onto a predetermined position in a discrete manner. Longer lifespan can be expected in the latter method than in the fixed focus method but the target similarly deteriorates.

When the target deteriorates, maintenance of the target needs to be carried out as the irradiated X-ray amount decreases and the X-ray image becomes dark, or the image quality lowers and the examination efficiency degrades. The deterioration of the target is limited to a small portion where the electron beam impinges, and thus the user performs the maintenance of the target by rotating the target surface. The position where the electron beam impinges shifts from the deteriorated position, and characteristics similar to a new target can be obtained.

For instance, when performing the X-ray examination using Micro-focus X-ray source L9191 manufactured by Hamamatsu Photonics K. K., the user carries out the maintenance of the target by manually rotating the target surface.

Generally, the lifetime of the target of the transmissive X-ray source is between about 300 hours to 500 hours. If the frequency of use is small as with an analyzer, the period until the target deteriorates is long and the trouble necessary for carrying out the maintenance of the target will not be a problem. However, if operated for a long period of time as with an in-line examination apparatus, the period until the target deteriorates is short, and thus it is important that the maintenance of the target is easy and convenient to carry out.

In a method of carrying out the maintenance by manually rotating the target, the maintenance workman needs to be familiar with the task and the task requires time. Information for maintenance, for example, how long and at which position of the target the X-ray is irradiated need to be managed.

In the method of repeatedly using a predetermined position of the target in a discrete manner in the scanning X-ray source, the electron beam is impinged on a plurality of positions, and thus the amount of information for maintenance becomes enormous, and becomes difficult for the user to manage.

SUMMARY OF THE INVENTION

In view of solving the above problems, it is an object of the present invention to provide an X-ray examination apparatus capable of efficiently using the target surface, and an X-ray examination method using the X-ray examination apparatus applied with an X-ray photographing method of the X-ray examination apparatus.

It is another object of the present invention to provide an X-ray examination apparatus capable of reducing the trouble necessary for carrying out maintenance of the X-ray source by uniformly using the target surface of the same target, and an X-ray examination method using the X-ray examination apparatus applied with the X-ray photographing method of the X-ray examination apparatus.

One aspect of the present invention relates to an X-ray examination method using an X-ray examination apparatus for examining an examining portion of an object by X-ray irradiation, the apparatus including a detection surface for detecting an intensity distribution of an X-ray set and entered to a position specified out of predetermined positions, an X-ray source capable of moving an X-ray focal position on a target surface and generating the X-ray, and a storage device for storing history information on generation of the X-ray at the position on the target surface as the X-ray focal position, the method including the steps of: setting the X-ray focal position corresponding to a position of the detection surface specified out of a plurality of first predetermined positions and the examining portion; detecting that an X-ray radiation dosage generated from the set X-ray focal position has exceeded a predetermined amount based on the history information of the storage device; changing and setting a specified position of the detection surface to one of a plurality of second predetermined positions different from the plurality of first predetermined positions according to the detection result; moving the X-ray focal position to a position reset according to the changed detection surface, and generating the X-ray; and detecting an intensity distribution of the X-ray transmitted through the examining portion on the detection surface.

Preferably, the step of setting the X-ray focal position includes a step of determining the X-ray focal position on the target surface so that the X-ray transmits through the examining portion and enters the detection surface.

Preferably, the step of changing and setting the specified position includes a step of specifying a plurality of detection surfaces for detecting the X-ray out of the plurality of second predetermined positions; the step of generating the X-ray includes steps of: determining each of the plurality of X-ray focal positions on the target surface so that the X-ray transmits through the examining portion and enters the plurality of detection surfaces, and moving an irradiating position applied with an electron beam of the X-ray source to the each determined X-ray focal position, and generating the X-ray; and the method further includes a step of: reconstructing image data of the examining portion based on data of the detected intensity distribution.

Preferably, the step of detecting that the X-ray radiation dosage has exceeded the predetermined amount includes a step of detecting that at least an accumulated time in which the X-ray is generated from the set X-ray focal position has elapsed a predetermined time.

Preferably, the step of determining each of the plurality of X-ray focal positions includes a step of determining the X-ray focal position excluding a position applied with the electron beam beyond the predetermined time.

Preferably, the step of determining each of the plurality of X-ray focal positions includes a step of determining the X-ray focal position out of a position applied with the electron beam beyond the predetermined time excluding a range determined based on an area coefficient corresponding to a size of an X-ray focus.

Preferably, the step of generating the X-ray includes a step of changing an irradiation position applied with an electron beam on the target surface by deflecting the electron beam, and moving the X-ray focal position.

Another aspect of the present invention relates to an X-ray examination apparatus for examining an examining portion of an object with X-ray, the X-ray examination apparatus including: an X-ray detector having a plurality of detection surfaces for detecting the X-ray, the X-ray detector including a detection position changing part for changing the positions of the plurality of detection surfaces from a plurality of first predetermined positions to a plurality of second predetermined positions different from the plurality of first predetermined positions; an output controller for controlling an output process of the X-ray, the output controller including: a starting point setting part for setting, on the plurality of detection surfaces, each starting point of X-ray emission so that the X-ray transmits through the examining portion of the object and enters the each detection surface, a storage part for storing the each starting position and history information on emission of the X-ray from the each starting position in correspondence to each other, and a detection part for detecting that an accumulated irradiation time has elapsed a predetermined time on the set starting point position based on the history information in the storage part, and outputting the detection result to allow the detection position changing part to change, the starting point setting part resets the each starting point position when change is made by the detection position changing part, the apparatus further including: an X-ray output part for moving an X-ray focal position of an X-ray source to the each starting position and generating the X-ray; and a reconstruction part for reconstructing image data of the examining portion based on data of an intensity distribution of the X-ray transmitted through the examining portion detected on the plurality of detection surfaces.

Preferably, the X-ray output part includes a part for deflecting an electron beam and moving an irradiation position on the target surface to move the X-ray focal position.

Preferably, the detection position changing part includes: a rotatable base arranged with the plurality of detection surfaces on a circumference having a predetermined axis as a center; and a rotating part for rotating the rotatable base with the axis as the center; wherein the positions of the plurality of detection surfaces are changed from the plurality of first predetermined positions to the plurality of second predetermined positions by rotating the rotatable base by a constant angle according to the detection result of the detection part.

Preferably, the starting point setting part sets the each starting point position excluding the position associated with an irradiation time that has elapsed the predetermined time based on the history information.

Preferably, the output part further includes a specifying part for specifying an examining portion of the object.

According to the X-ray examination apparatus and the examination method of the X-ray examining apparatus of the present invention, the target surface can be efficiently used.

BRIEF DESCRIPTION OF THE DRAWINGS

FIGS. 3A and 3B show views of a sensor base 22 when seen from the scanning X-ray source 10 side;

FIG. 9 shows a view showing currently used target maintenance information;

FIG. 10 shows a view showing previously used target maintenance information;

FIG. 11 shows a view showing NG target maintenance information;

DETAILED DESCRIPTION OF THE PREFERRED EMBODIMENTS

Figure 1:
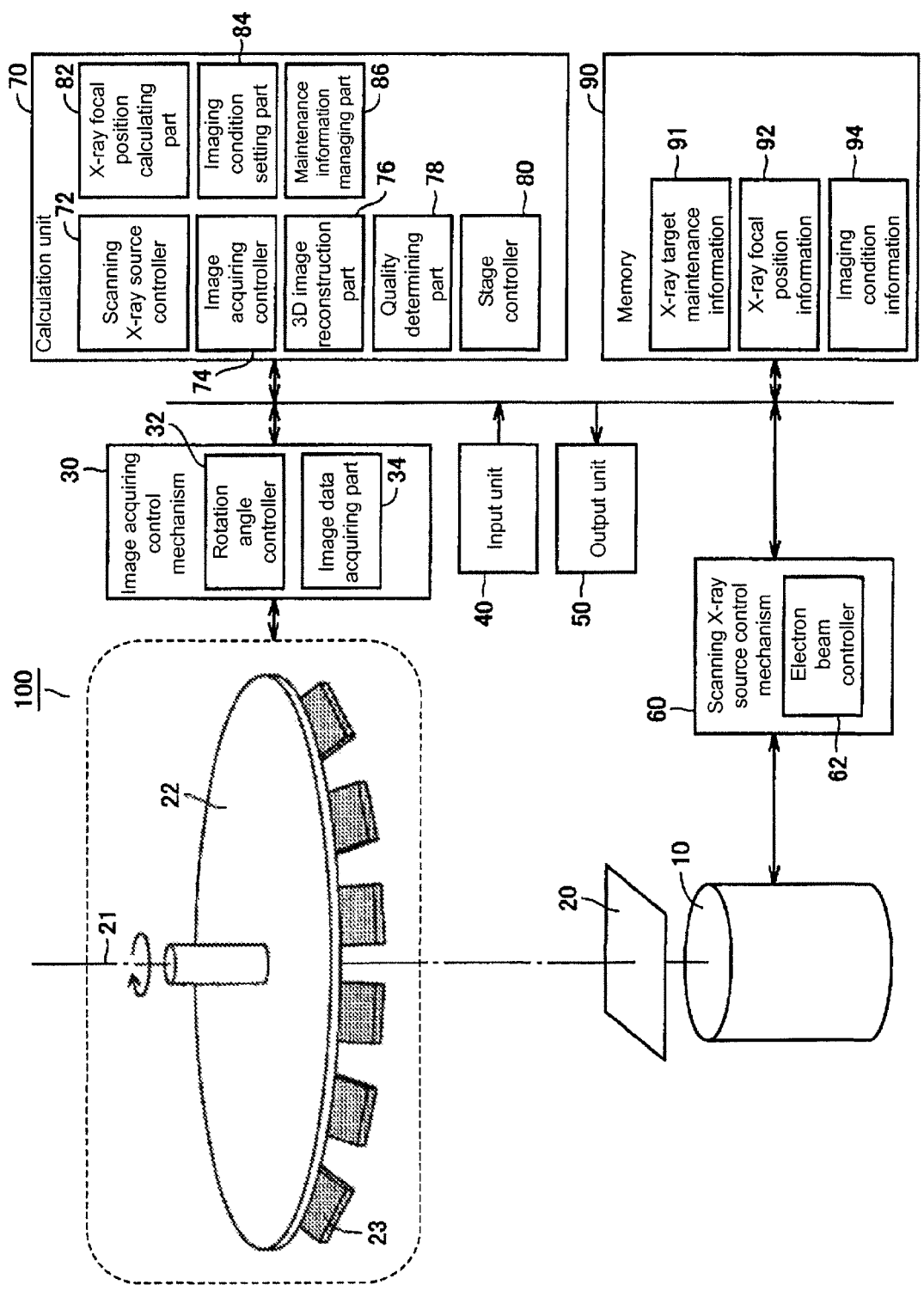
FIG. 1 shows a schematic block diagram of an X-ray examination apparatus 100 according to the present invention.

Embodiments of the present invention will be described with reference to the drawings. In the following description, same reference numerals are denoted for the same components. The names and the functions thereof are also the same. Therefore, detailed description thereon will not be repeated.

(1. Configuration of the Present Invention)

FIG. 1 shows a schematic block diagram of an X-ray examination apparatus 100 according to the present invention.

The X-ray examination apparatus 100 according to the present invention will be described with reference to FIG. 1. It should be noted that configuration, dimension, shape, and other relative arrangements described below do not intend to exclusively limit the scope of the invention thereto unless specifically stated.

The X-ray examination apparatus 100 includes a scanning X-ray source 10 for outputting X-rays, and a sensor base 22 being attached with a plurality of X-ray sensors 23 and being a rotatable base that rotates with a rotation axis 21 as a center. An examining target 20 is arranged between the scanning X-ray source 10 and the sensor base 22. The X-ray examination apparatus 100 also includes an image acquiring control mechanism 30 for controlling acquisition of rotation angle about the rotation axis of the sensor base 22 and image data from the X-ray sensor 23; an input unit 40 for accepting instruction input etc. by a user; and an output unit 50 for outputting measurement result etc. to the outside. The X-ray examination apparatus 100 furthermore includes a scanning X-ray source control mechanism 60, a calculation unit 70, and a memory 90. In such a configuration, the calculation unit 70 executes a program (not shown) stored in the memory 90 to control each unit, and performs a predetermined calculation process.

The scanning X-ray source 10 is controlled by the scanning X-ray source control mechanism 60, and irradiates X-rays to the examining target 20.

Figure 2:
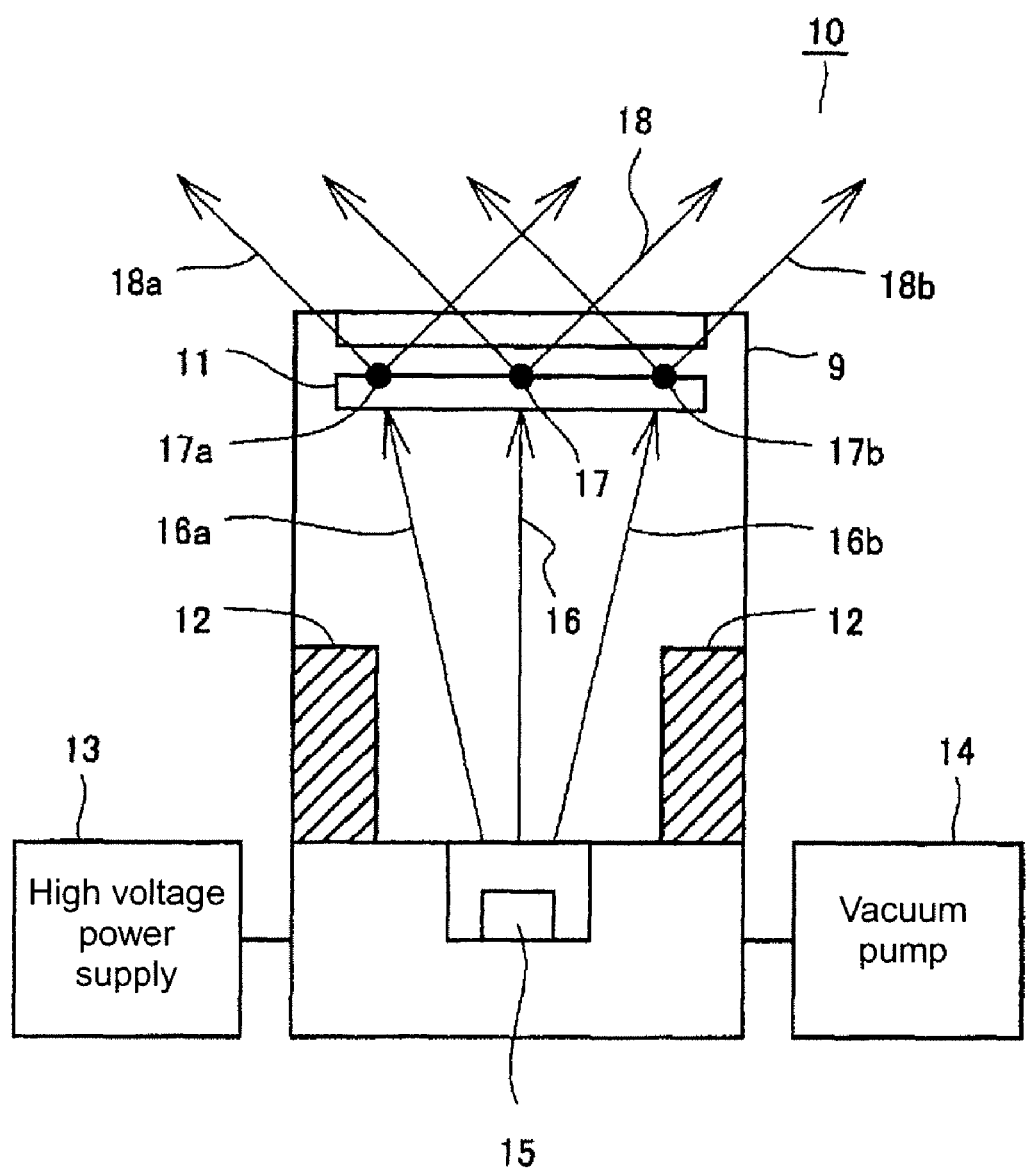
FIG. 2 shows a cross sectional view showing a configuration of a scanning X-ray source 10.

FIG. 2 shows a cross sectional view showing a configuration of the scanning X-ray source 10.

With reference to FIG. 2, an electron beam 16 is irradiated to a target 11 such as tungsten from an electron gun 15 controlled by an electron beam controller 62 in the scanning X-ray source 10. An X-ray 18 is generated at a site (X-ray focal position 17) where the electron beam 16 impinges the target, and is emitted (output). The electron beam system is accommodated in a vacuum container 9. The inside of the vacuum container 9 is maintained in vacuum by a vacuum pump 14, and the electron beam 16 accelerated by a high voltage power supply 13 is emitted from the electron gun 15.

In the scanning X-ray source 10, the site where the electron beam 16 impinges the target 11 can be arbitrarily changed by deflecting the electron beam 16 by means of a deflection yoke 12. For instance, an electron beam 16a deflected by the deflection yoke 12 impinges the target 11, and an X-ray 18a is output from an X-ray focal position 17a. Similarly, an electron beam 16b deflected by the deflection yoke 12 impinges the target 11, and an X-ray 18b is output from an X-ray focal position 17b. In the present invention, the scanning X-ray source 10 is of a transmissive type, and a target not in a ring shape but a target having a continuous surface is desirable so that, when generating the X-ray from a position (hereinafter referred to as "starting position of X-ray emission") to become the starting position of X-ray emission set according to the examining target portion of the examining object, the degree of freedom in setting such a position can be enhanced, as hereinafter described. In the following description, the position is simply referred to as the X-ray focal position 17 as a collective term unless the position is particularly distinguished.

The position of the X-ray source itself can also be mechanically moved each time when moving the X-ray focal position to the each starting position of X-ray emission. However, with the configuration shown in FIG. 2, when moving the X-ray focal position to the starting position of X-ray generation within a constant range, the X-ray source does not need to be mechanically moved, whereby it is possible to realize an X-ray examination apparatus excelling in maintenance and reliability. Alternatively, a plurality of X-ray sources may be arranged so as to be switched in time of use according to the starting position.

The size of the X-ray focus formed when the electron beam 16 impinges the target 11 is generally from one sub-micron to a few hundred microns. When the electron beam impinges the same position of the target 11 for greater than or equal to a predetermined time, the relevant position and a predetermined range with such a position as the center deteriorate through thermal damage and the like. When the X-ray focal position deteriorates, the irradiated X-ray amount decreases and the X-ray image becomes darker, or the image quality lowers and the examination efficiency degrades.

In the method of the prior art, the target 11 itself is rotated etc. so that the target of the X-ray focal position has the same characteristics as the new target in order to prevent lowering in image quality etc. However, this method takes time in the rotation task and needs to interrupt the X-ray examination.

In the present invention, the position of each X-ray sensor 23 is changed, and the starting position of X-ray emission that becomes the X-ray focal position 17 is newly set so that the X-ray enters each X-ray sensor 23 after the position is changed. The scanning X-ray source 10 according to the present invention deflects the electron beam 16 to easily change the position the electron beam 16 impinges the target 11 to an arbitrary location, and thus the irradiating position of the electron beam can be moved according to an accumulative irradiation time on the target 11, and the maintenance of the target can be carried out without interrupting the X-ray examination.

Returning back to FIG. 1, the scanning X-ray source control mechanism 60 includes an electron beam controller 62 for controlling the output of the electron beam. The electron beam controller 62 receives a specification of X-ray focal position, X-ray energy (tube voltage, tube current) from the calculation unit 70. The X-ray energy differs depending on the configuration of the examining target.

The examining target 20 is arranged between the scanning X-ray source 10 and the X-ray sensor 23 (sensor base 22). The examining target 20 may be moved to an arbitrary position in X-Y-Z stage, or may be arranged at a position for examination by moving in one direction like a belt conveyor. If the examining target is small as in print mounting substrate, the examining target is moved with the scanning X-ray source 10 and the sensor base 22 fixed, but if the examining target is difficult to be arbitrarily moved since the examining target such as a glass substrate has a large area, the scanning X-ray source 10 and the sensor base 22 are moved with the relative position of the scanning X-ray source 10 and the sensor base 22 fixed.

The X-ray sensor 23 is a two-dimensional sensor for detecting and imaging an X-ray output from the scanning X-ray source 10 and transmitted through the examining target 20. The X-ray sensor 23 may be a CCD (Charge Coupled Device) camera, I.I. (Image intensifier) tube, and the like. In the present invention, an FPD (Flat Panel Display) having satisfactory space efficiency is desirable since a plurality of X-ray sensors is arranged in the sensor base 22. High sensitivity is also desirable so that use can be made in an in-line examination, and the FPD of direct conversion method using CdTe is particularly desirable. In the following description, the sensor is simply referred to as the X-ray sensor 23 as a collective term unless the sensor is particularly distinguished.

In the sensor base 22, the plurality of X-ray sensors 23 are attached on a circumference of the rotatable base on the scanning X-ray source 10 side. The sensor base 22 can rotate with the rotation axis 21 of the rotatable base as the center.

Actually, the rotatable range only needs to be less than or equal to one rotation, and when N X-ray sensors are arranged on the circumference of the sensor base 22, the angle formed by the adjacent X-ray sensors and the center of rotation of the sensor base only needs to rotate about 360/N. Obviously, this equation is merely one specific example, and the rotation angle is not limited by such an equation. The rotation angle of the sensor base 22 is known by a sensor (not shown), and is retrieved to the calculation unit 70 via the input unit 40.

The sensor base 22 is desirably raised and lowered in the up and down direction to adjust the scale of enlargement. In this case, the position of the sensor base 22 in the up and down direction is known by a sensor (not shown), and is retrieved to the calculation unit 70 by the input unit 40. The angle of the X-ray entering the X-ray sensor 23 changes when the sensor base 22 is raised and lowered in the up and down direction, and thus the inclination angle with respect to the sensor base 22 of the X-ray sensor 23 is desirably controllable.

The image acquiring control mechanism 30 includes a rotation angle controller 32 for performing a control so that the sensor base rotates at an angle specified by the calculation unit 70, and an image data acquiring part 34 for acquiring image data of the X-ray sensor 23 specified by the calculation unit 70. The X-ray sensor specified by the calculation unit 70 may be one or may be in plurals.

The input unit 40 is an operation input equipment for accepting input of a user. The output unit 50 is a display for displaying X-ray image etc. configured with the calculation unit 70 and information for maintenance of the target.

That is, the user executes various inputs through the input unit 40, and various calculation results obtained by the processes of the calculation unit 70 are displayed on the output unit 50. The image displayed on the output unit 50 may be output for visible quality determination by the user or may be output as quality determination result of a quality determination part 78 to be hereinafter described.

The calculation unit 70 includes a scanning X-ray source controller 72, an image acquiring controller 74, a 3D image reconstruction part 76, a quality determination part 78, a stage controller 80, an X-ray focal position calculating part 82, an imaging condition setting part 84, and a maintenance information managing part 86.

The scanning X-ray source controller 72 determines the X-ray focal position and the X-ray energy, and sends a command to the scanning X-ray source control mechanism 60.

The image acquiring controller 74 determines a rotation angle of the sensor base 22 and the X-ray sensor 23 to acquire the image, and sends a command to the image acquiring control mechanism 30. The image is acquired from the image acquiring control mechanism 30.

The 3D image reconstruction part 76 reconstructs three-dimensional data based on a plurality of data acquired by the image acquiring controller 74.

The quality determination part 78 determines the quality of the examining target based on 3D image data reconstructed by the 3D image reconstruction part 76 or perspective data. For instance, quality determination can be performed by recognizing the shape of a solder ball, and determining whether or not the shape is within a tolerable range defined in advance. An algorithm for performing quality determination or input information to the algorithm differ depending on the examining target and are available from the imaging condition information 94.

The stage controller 80 controls a mechanism (not shown) for moving the examining target 20. The X-ray focal position calculating part 82 calculates the X-ray focal position, irradiation angle, and the like with respect to an examination area when examining a certain examination area of the examining object 20. The details thereof will be hereinafter described.

The imaging condition setting part 84 sets the conditions for a case of outputting the X-ray from the scanning X-ray source 10 according to the examining target 20. The conditions include an application voltage on the X-ray tube, and imaging time.

The maintenance information managing part 86 accumulates the time the electron beam is irradiated onto the target surface, and determines the X-ray focal position where the accumulative irradiation time has elapsed a predetermined threshold value (time representing lifetime of target) as a focal position that cannot be used as the starting position of X-ray emission. The lifetime of the target is notified to the user through alarm display etc. via the output unit 50.

In the present embodiment, the lifetime of the target is determined with the irradiation time of the electron beam by way of example, but may be determined by the user by looking at the perspective image, or more generally, determined based on the X-ray generation amount.

The lifetime of the target can be determined based on the X-ray generation amount with a method of assuming the intensity of the X-ray as a group of X-ray photons, or a method of analyzing the number of X-ray photons and the energy thereof.

In the method of assuming the intensity of the X-ray as a group of photons, the decreasing rate of dosage (integrated dosage µSV, dosage per hour µSv/h) is determined using a dosemeter such as an ionization chamber.

In the method of analyzing the number of X-ray photons and energy thereof, a profile of the X-ray generation amount in a desired target state (not reaching lifetime) (e.g., horizontal axis is energy of X-ray photon, vertical axis is number of photons) is obtained using a semiconductor X-ray detector etc., and determination is made based on change in the profile. For instance, determination is made that the lifetime is over when a shift amount exceeds a certain threshold value or when the decreasing rate of intensity (the number of photons) of the X-ray energy, which is important in examination, exceeds a threshold value.

The memory 90 includes X-ray target maintenance information 91 storing information provided by the maintenance information managing part 86, X-ray focal position information 92 storing information related to the X-ray focal position calculated by the X-ray focal position calculating part 82, and imaging condition information 94 storing imaging condition set by the imaging condition setting part 84 and algorithm for performing quality determination.

The X-ray target maintenance information 91 includes currently used target maintenance information in which the X-ray focal position currently being used in imaging and the accumulated X-ray irradiation time or the accumulation of the time the electron beam is irradiated on the X-ray focal position are corresponded to each other, previously used target maintenance information in which the X-ray focal position used in the past in imaging and the accumulated X-ray irradiation time of the X-ray focal position are corresponded to each other, and NG target maintenance information indicating the position of the target surface that cannot be used as the X-ray focal position.

The X-ray target maintenance information 91 contains an area coefficient D corresponding to the size of the X-ray focus. As mentioned above, the size of the X-ray focus is generally one sub-micron to a few hundred microns, but actually, the surrounding area of the focus size is also subjected to damages such as thermal damage. The area coefficient D is thus set. The maintenance information managing part 86 determines a range of diameter D or diagonal D with the X-ray focal position as the center as the portion that is subjected to damage in the target and that cannot be used (lifetime is over) as the focal position of the X-ray.

With respect to each examination area, the X-ray focal position information 92 is associated with the calculation result (focal position, irradiation angle, sensor imaging angle, sensor arrangement angle, sensor inclination angle, etc. with respect to each X-ray sensor 23) calculated by the X-ray focal position calculating part 82. This will be hereinafter specifically described.

The memory 90 merely needs to be able to store data, and is configured by storage devices such as a RAM (Random Access Memory) and an EEPROM (Electrically Erasable and Programmable Read-Only Memory).

FIG. 3 shows a view of the sensor base 22 when seen from the scanning X-ray source 10 side. In particular, FIG. 3A shows a view in which the X-ray sensors 23 arranged on the same radius, and FIG. 3B shows a view in which the X-ray sensors 23 are arranged on different radii.

The sensor base 22 will be described with reference to FIG. 3. A plurality of X-ray sensor modules 25 in which a mechanism component for performing data processing etc. is compounded to the X-ray sensor 23 is attached to the sensor base 22. The X-ray sensor module 25 may be arranged so that the X-ray sensor 23 is on the circumference of the same radius of a circle having the center of rotation of the sensor base as a center, as shown in FIG. 3A, or may be arranged on a circumference of different radii, as shown in FIG. 3B. The sensor module 25 is desirably also arranged at the center of the sensor base 22. The X-ray sensor module 25 is desirably controlled so as to be freely movable in a radial direction by way of a slider 24. The imaged data of the examining target when seen from various degrees then can be acquired.

Figure 4:
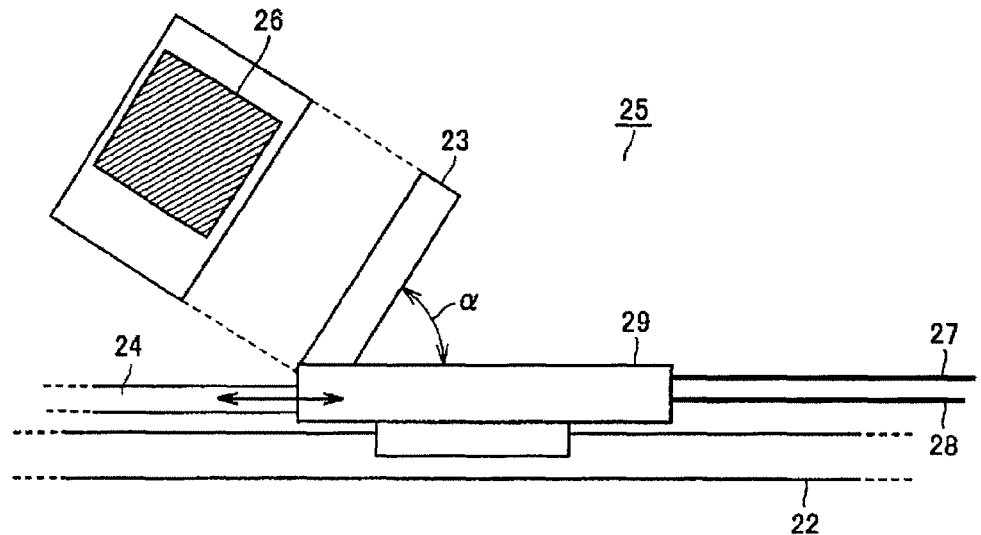
FIG. 4 shows a side view showing an X-ray sensor module 25.

FIG. 4 shows a side view showing the X-ray sensor module 25. A view of the X-ray sensor 23 when seen from an X-ray receiving part 26 side is also shown.

The X-ray sensor module 25 will be described with reference to FIG. 4. The X-ray sensor module 25 includes the X-ray receiving part 26 for converting the X-ray to an electrical signal, and a data processing part 29 for creating data of the electrical signal and transmitting the data to the image data acquiring part 34 through a data cable 27. Power is externally supplied to the X-ray sensor module 25 via a power supply cable 28. The X-ray sensor module 25 can be freely moved in a radial direction by way of the slider 24, but may be fixed at a position.

The X-ray sensor 23 is inclined by a constant angle (sensor inclination angle $\alpha$) with respect to the sensor base 22. In FIG. 4, the sensor inclination angle $\alpha$ is fixed, but angular adjustment may be carried out according to the control by the image acquiring control mechanism 30.

The plurality of X-ray sensor modules 25 are attached to the sensor base 22, but are respectively removable. Therefore, only the damaged X-ray sensor module can be replaced.

Figure 5:
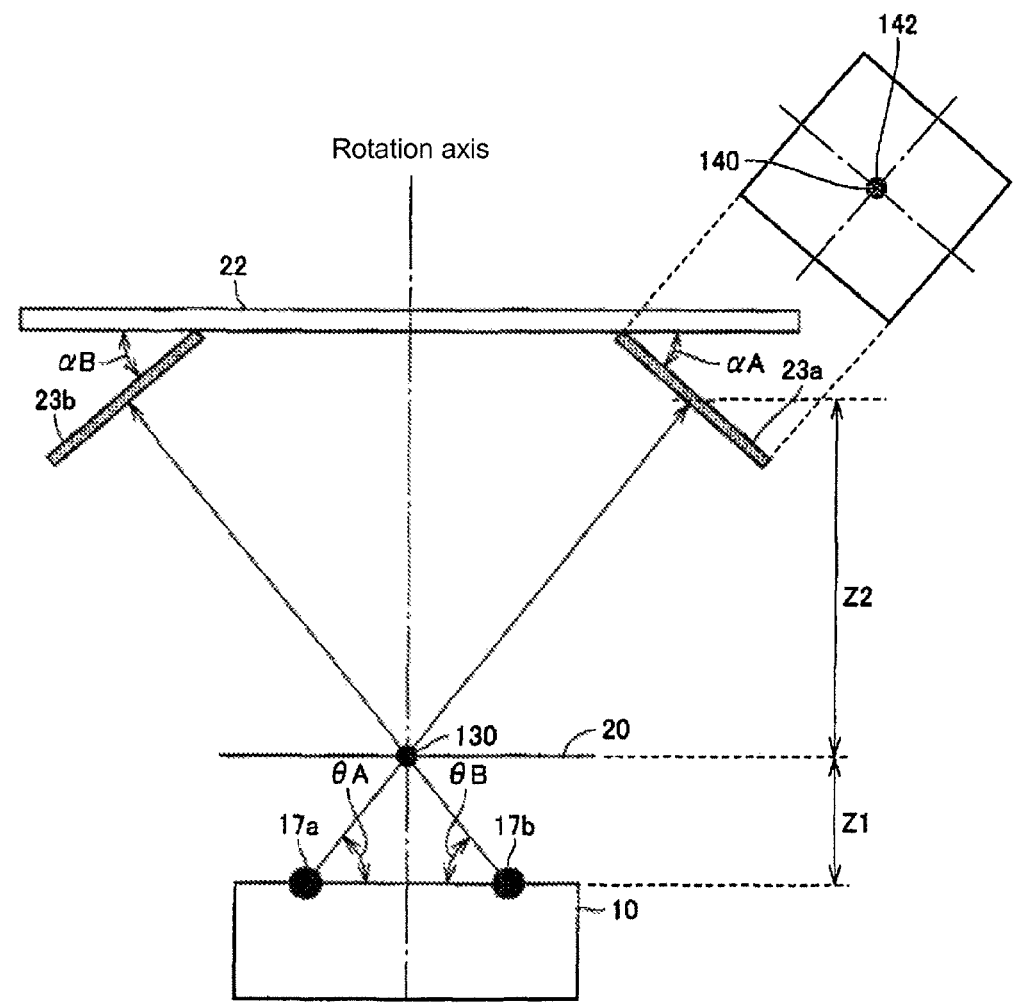
FIG. 5 shows a conceptual view of an imaging system seen from the side.

FIG. 5 shows a conceptual view of an imaging system seen from the side.

The imaging system will be described with reference to FIG. 5. In FIG. 5, the X-ray sensors 23a, 23b may be any X-ray sensor 23 as long they are in an opposing position relationship. In FIG. 5, the X-ray sensors 23a, 23b are respectively inclined by a constant angle (sensor inclination angle $\alpha A$, $\alpha B$) with respect to the sensor base 22. Suppose a distance Z1 is from the target surface of the scanning X-ray source 10 to the examining target 20, and distance Z2 is from the examining target 20 to the X-ray sensor 23.

In FIG. 5, a work 130 is on the rotation axis of the sensor base 22. When imaging the work 130, a position (starting position of X-ray emission) at which the focal position (irradiating position of electron beam) of the X-ray output from the scanning X-ray source 10 to the X-ray sensor 23 is to be set is determined. For instance, an X-ray focal position 17a with respect to the X-ray sensor 23a is set at an intersection of a line connecting the sensor center 140 of the X-ray sensor 23a and the center of the work (examination area) 130 and the target surface of the scanning X-ray source 10. A perspective image 142 of the work is detected at the sensor center 140. That is, the starting position of X-ray emission is set such that the X-ray transmits through the work and enters the detection surface with respect to the detection surface of the corresponding X-ray sensor. Therefore, the sensor center 140 of the X-ray sensor 23a, the center of the work 130, and the X-ray focal position 17a are desirably lined on the same line, but the arrangement is not limited to such an arrangement as long the X-ray enters within a constant range of the detection surface.

Suppose an angle formed by the line connecting the X-ray sensor 23 and the X-ray focal position 17 and the target surface of the scanning X-ray source 10 is an irradiation angle $\theta$. For instance, the irradiation angles $\theta A$, $\theta B$ are formed with respect to the X-ray sensors 23a, 23b, respectively. The angle is simply referred to as irradiation angle $\theta$ unless each irradiation angle is particularly distinguished.

As shown in FIG. 5, when the works exists on a perpendicular line of the center of rotation of the sensor base, the irradiation angle $\theta$ for all the X-ray sensors 23 becomes equal. In the present invention, the work does not need to be on the center of rotation of the sensor base, and thus each irradiation angle is not necessarily equal to each other.

Figure 6A:
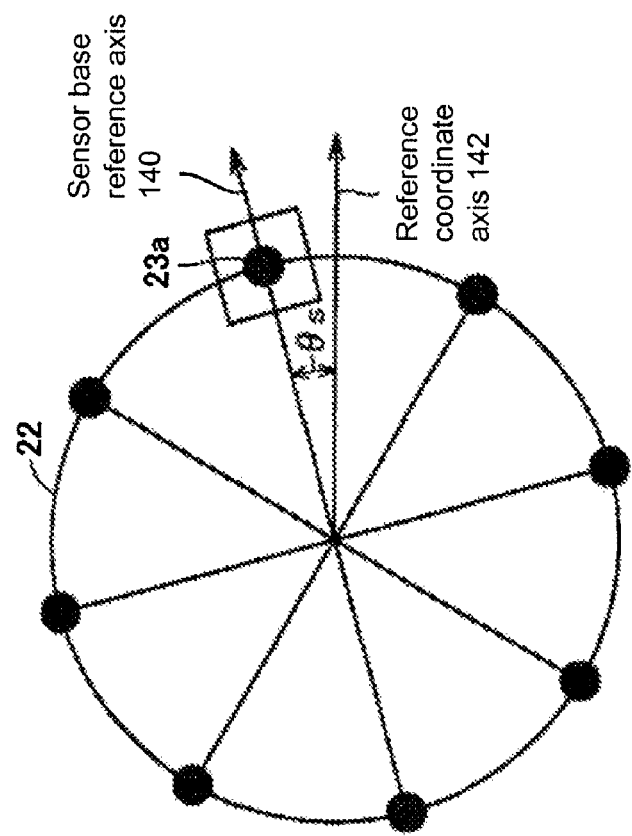
FIGS. 6A and 6B show views describing a sensor arrangement angle and a sensor base reference angle.
Figure 6B:
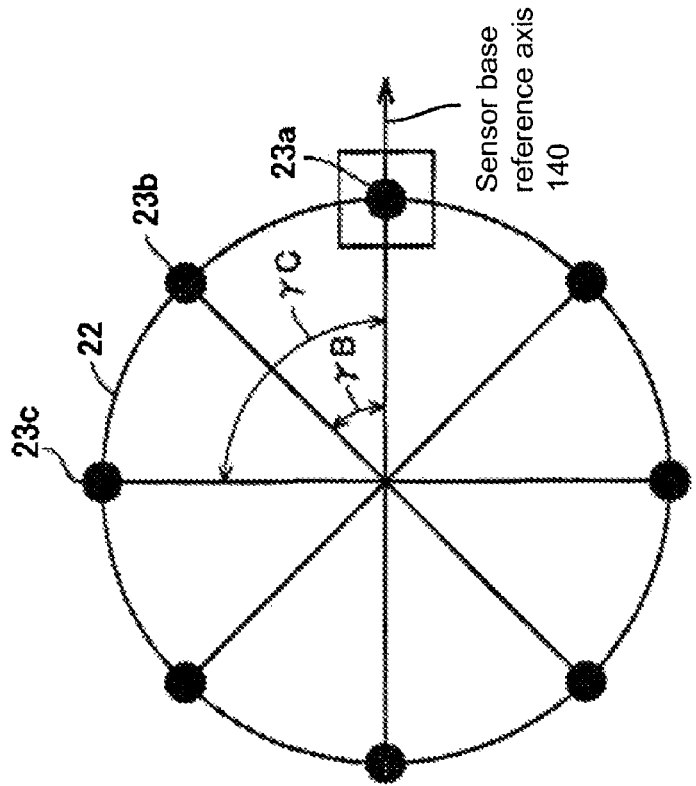

FIG. 6 shows a view describing the sensor arrangement angle and a sensor base reference angle. In particular, FIG. 6A shows a view of before the sensor base is rotated, and FIG. 6B shows a view of after the sensor base is rotated by $\theta s$.

The sensor arrangement angle and the sensor base reference angle will be described with reference to FIG. 6. In FIG. 6, the X-ray sensors 23a, 23b, 23c may be any X-ray sensor 23 as long as a relationship in which the X-ray sensors 23a, 23b are arranged so as to be adjacent to the X-ray sensor 23b on the circumference of the sensor 22 is obtained.

As shown in FIG. 6A, a sensor base reference axis 140 that acts as a reference when indicating the position relationship with respect to the X-ray sensors 23 is defined in the sensor base 22. Here, an axis connecting the X-ray sensor 23a and the sensor 22 is the sensor base reference axis 140.

Suppose an angle formed by the X-ray sensor 23 and the sensor base reference axis 140 is the sensor arrangement angle $\gamma$. For instance, the sensor arrangement angles $\gamma B$, $\gamma C$ are formed with respect to the X-ray sensors 23b, 23c, respectively. The angle is simply referred to as sensor arrangement angle $\gamma$ unless each sensor arrangement angle is particularly distinguished.

As shown in FIG. 6B, suppose an axis corresponding to a position of the sensor base reference axis 140 in FIG. 6A is a reference coordinate axis 142. The reference coordinate axis 142 is an axis that becomes a reference when rotating the sensor base 22 for imaging. An angle formed by the reference coordinate axis 142 and the sensor base reference axis 140 is the sensor base reference angle $\theta s$. In the case of FIG. 6A, the sensor reference angle is zero degrees.

Figure 7B:
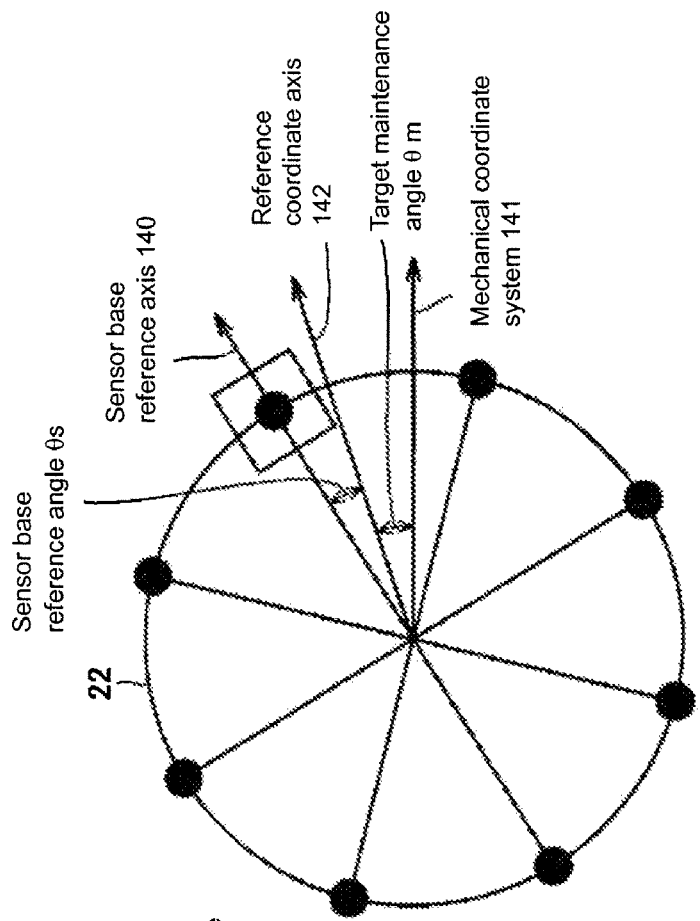
FIGS. 7A and 7B show views describing a target maintenance angle.
Figure 7A:
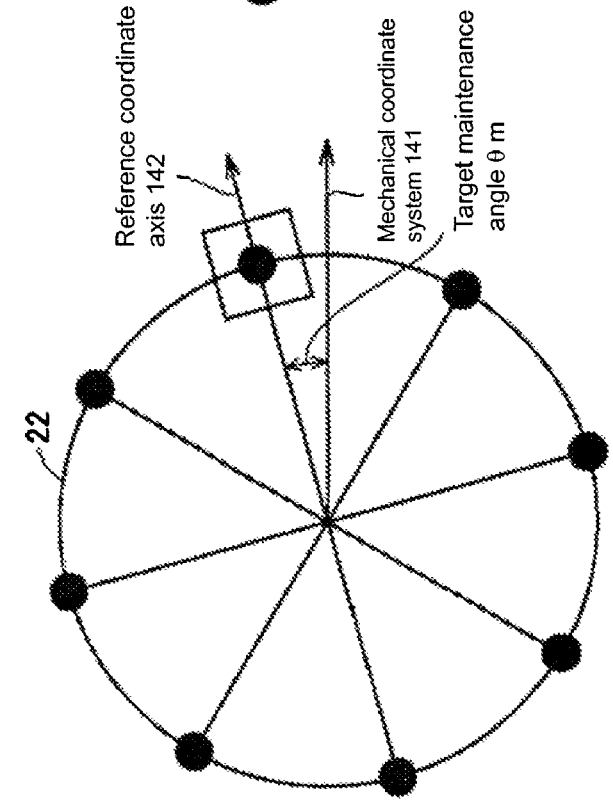

FIG. 7 shows a view describing a target maintenance angle. In particular, FIG. 7A shows a view of after the reference coordinate axis is rotated by $\theta m$ with respect to a mechanical coordinate system, and FIG. 7B shows a view of after the sensor base reference angle is rotated by θs with respect to the reference coordinate axis.

The target maintenance angle will now be described with reference to FIG. 7.

As shown in FIG. 7A, a mechanical coordinate system 141, which is a coordinate system fixed in the sensor base 22 and used when indicating an absolute position of each X-ray sensor 23, is defined in the sensor base 22. The mechanical coordinate system 141 acts as a reference when rotating the sensor base 22 to shift the X-ray focal position at the target 11. The angle formed by the reference coordinate axis 142 and the mechanical coordinate system 141 is the target maintenance angle θm.

As shown in FIG. 7B, the sensor base reference axis 140 is rotated with respect to the reference coordinate axis 142 when rotating the sensor base 22 for imaging after rotation of target maintenance angle θm. As described above, the angle formed by the reference coordinate axis 142 and the sensor base reference axis 140 is the sensor base reference angle θs.

Figure 8:
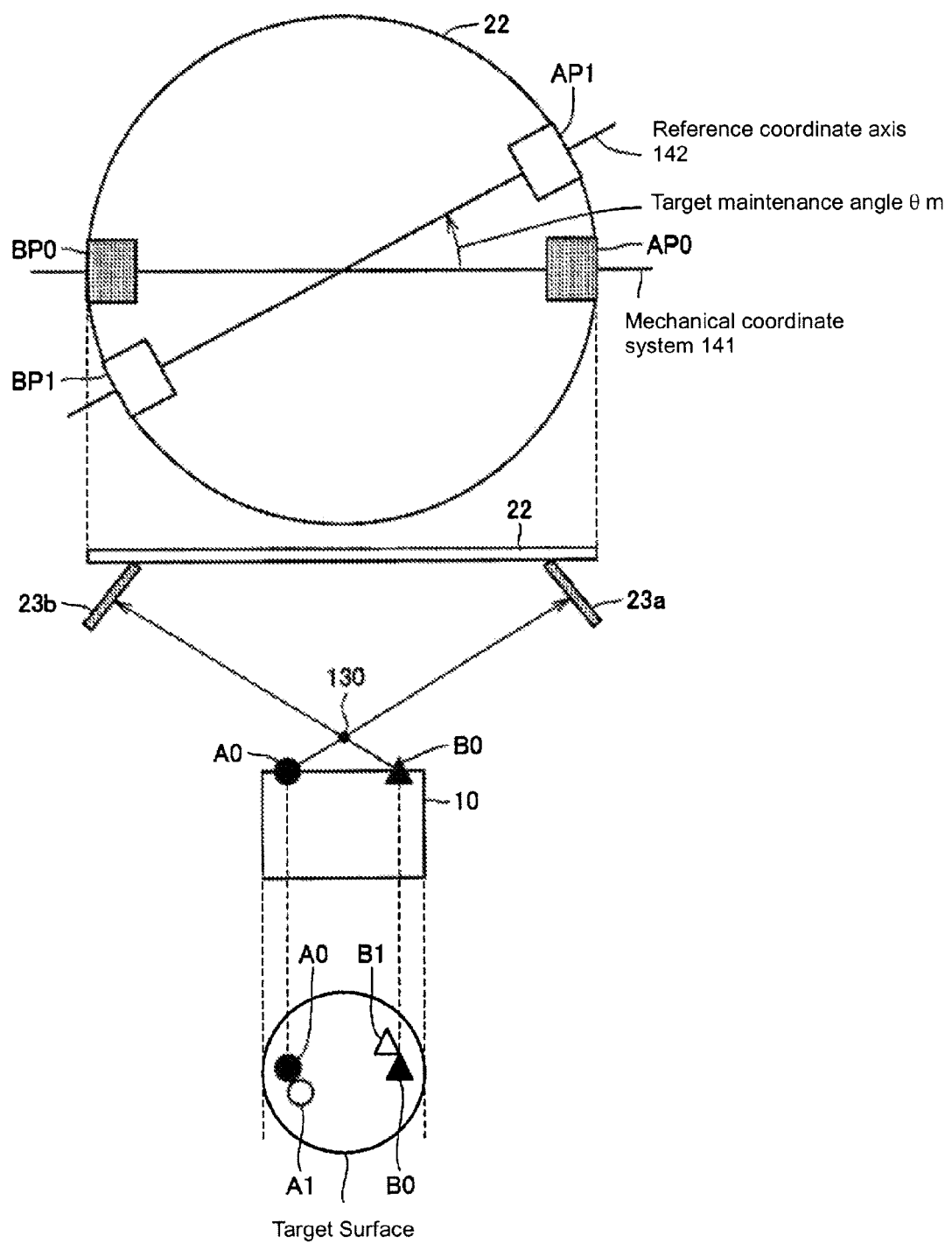
FIG. 8 shows a conceptual view of the imaging system seen from above and from the side, showing an image at rotating the sensor base 22.

FIG. 8 shows a conceptual view of the imaging system seen from above and from the side, showing an image at rotating the sensor base 22. A view of the scanning X-ray source 10 seen from the sensor base 22 side is also shown.

The relationship between the position of the X-ray sensor and the X-ray focal position when the sensor base 22 is rotated will be described with reference to FIG. 8.

As shown in FIG. 8, the X-ray focal position with respect to the X-ray sensor 23a is A0 and the X-ray focal position with respect to the X-ray sensor 23b is B0 before the sensor base 22 is rotated. In this case, the X-ray sensors 23a, 23b are at positions of AP0, BP0 when the sensor base 22 is seen from above.

When the sensor base 22 is rotated by the target maintenance angle θm, the X-ray sensors 23a, 23b are at positions of AP1, BP1 when the sensor base 22 is seen from above.

As described in FIG. 5, after the rotation of the sensor base 22, the X-ray focal position newly set with respect to the X-ray sensor 23a at the position AP1 is A1, and the X-ray focal position newly set with respect to the X-ray sensor 23b at the position BP1 is B1.

Therefore, when the sensor base 22 is rotated, the position of the X-ray sensor 23 changes, and the X-ray focal position with respect to the X-ray sensor 23 also changes.

FIG. 9 shows a view showing currently used target maintenance information.

The currently used target maintenance information contained in the X-ray target maintenance information 91 will be described with reference to FIG. 9.

In the currently used target maintenance information 200, an X-ray focal position 202 indicating the focal position of the X-ray used in imaging at the current time and an accumulated X-ray irradiation time 204 indicating the accumulated time the electron beam is irradiated on the relevant X-ray focal position are corresponded to each other.

FIG. 10 shows a view showing previously used target maintenance information.

The previously used target maintenance information contained in the X-ray target maintenance information 91 will be described with reference to FIG. 10.

In the previously used target maintenance information 210, an X-ray focal position 212 indicating the focal position of the X-ray used in imaging in the past and an accumulated X-ray irradiation time 214 indicating the accumulated time the electron beam is irradiated on the relevant X-ray focal position are corresponded to each other.

When the examining target or the examination area is changed, the information on the current X-ray focal position indicated by the currently used target maintenance information is stored in the previously used target information.

FIG. 11 shows a view showing NG target maintenance information.

The NG target maintenance information will be described with reference to FIG. 11.

In the NG target maintenance information 220, an X-ray focal position 222 indicating a position that cannot be used as the X-ray focal position on the target surface, an accumulated X-ray irradiation time indicating the accumulated time the electron beam is irradiated on the relevant X-ray focal position, and an automatic determination flag 226 indicating whether the NG target is automatically decided are corresponded to each other.

In the automatic determination flag 226, "ON" is indicated for the X-ray focal position that has been decided that the lifetime is over as the accumulated X-ray irradiation time has exceeded a predetermined threshold value by the maintenance information managing part 86 of the calculation unit 70. "OFF" is indicated for the X-ray focal position that has been decided that the lifetime is over by the user based on perspective image etc.

The X-ray examination process described in the next section is then performed using the X-ray examination apparatus 100 having the above configuration.

(2. Flow of X-Ray Examination Process)

The X-ray examination apparatus 100 according to the present embodiment performs a lifetime determination on the focal position of the target surface when performing the following X-ray examination process.

Figure 12:
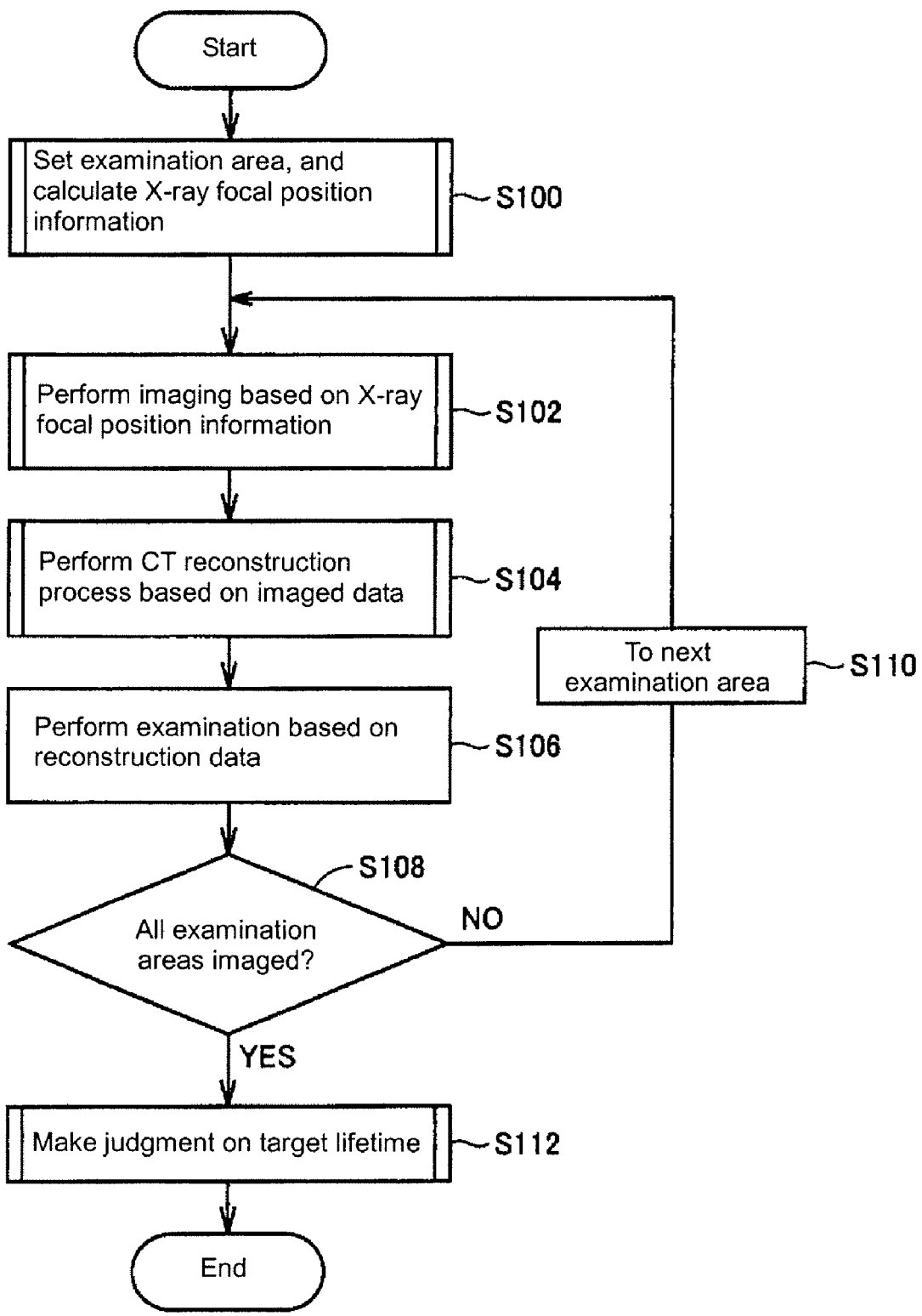
FIG. 12 shows a flowchart showing an outline of an X-ray examination process of the X-ray examination apparatus 100.

FIG. 12 shows a flowchart showing an outline of the X-ray examination process of the X-ray examination apparatus 100. The outline of the X-ray examination process will be described with reference to FIG. 12. The details of steps S100, 102, 104, and 112 will be hereinafter described. This flowchart is merely an example of the X-ray examination process, and may be executed with the steps interchanged.

First, in step S100, the examination area is set with respect to the examining target, and the X-ray focal position information is calculated. The examination area may be arbitrarily set by the user through the input unit 40, or may be set referencing the information on the examination area set in advance. A plurality of examination areas may be set. The calculation unit 70 calculates the X-ray focal position information.

In step S102, imaging is carried out based on the X-ray focal position information. Here, the process may proceed to the process of step S104 after all the imaging process is completed with respect to each X-ray sensor 23, or steps S102 and S104 may be performed in parallel in which case the imaged image data is sequentially provided for the process of step S104.

Subsequently, in step S104, back projection is performed based on the plurality of image data to a three-dimensional reconstruction space to generate reconstruction data and obtain a CT image according to the CT algorithm.

In step S106, examination is carried out based on the reconstruction data. The examination includes a case where the user performs the examination with the reconstruction data displayed on a display etc., and a case where decision is automatically made based on the reconstruction data.

Lastly, in step S108, the calculation unit 70 determines whether or not imaging of all the examination areas set in step S100 is terminated. If determined that the imaging of all the examination areas is not terminated (NO in step S108), the examination area to be imaged is changed to the next set examination area in step S110, and the process returns to the process of step S102.

If determined that the imaging of all the examination areas is terminated (YES in step S108), the calculation unit 70 makes a judgment on the lifetime of the target of the X-ray focal position currently used in imaging in step S112, and terminates the process.

The timing for making the judgment on the lifetime of the target may be any timing as long as the X-ray examination apparatus is being used, and does not necessarily need to be performed after step S108.

Figure 13:
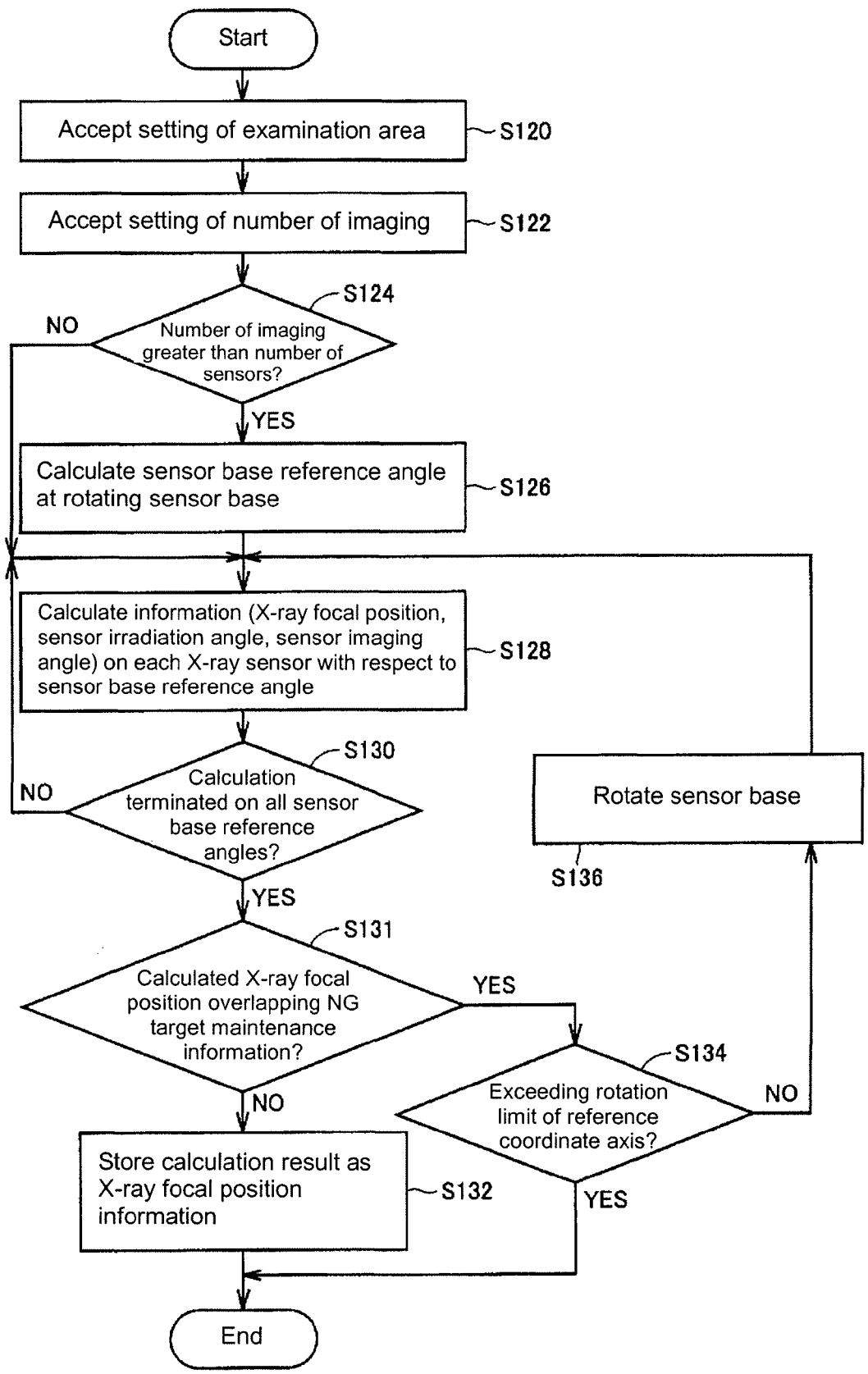
FIG. 13 shows a flowchart describing the process in step S100 of FIG. 12.

FIG. 13 shows a flowchart describing the process in step S100 of FIG. 12.

The details of the process in step S100 of FIG. 12 will be described with reference to FIG. 13. In step S120, the input unit 40 accepts the setting of the examination area by the user. The location (e.g., position coordinate) of the examination area is then provided to the X-ray focal position calculating part 82.

In step S122, the input unit 40 accepts the setting of number of imaging by the user. The number of imaging is then provided to the X-ray focal position calculating part 82. The number of imaging may be automatically set by the imaging condition setting part 84 according to the examining target and the examining item, or may be arbitrarily set by the user. In the present embodiment, the number of imaging is an integral multiples of the number of X-ray sensors attached to the circumference of the sensor base.

Subsequently, in step S124, the X-ray focal position calculating part 82 determines whether or not the set number of imaging is greater than the number of X-ray sensors attached to the circumference of the sensor base.

If determined that the number of imaging is greater than the number of X-ray sensor (YES in step S124), the X-ray focal position calculating part 82 calculates the sensor base reference angle at rotating the sensor base in step S126.

If there are n X-ray sensors 23, and the number of imaging is n×m (m is an integer greater than or equal to 2), m sensor base reference angles are calculated. Specifically, the sensor base angle is 0 degree, 360/n/m degrees, . . . , (360/n/m)×x degrees (x=1, . . . , m−1).

For instance an example of n=18, m=10 will be described by way of an example. In this case, the number of imaging is 18×10=180. The second sensor base reference angle is 360/18/10=2 degrees, and the last sensor base reference angle is (360/18/10)×9=18 degrees.

If determined that the number of image is less than the number of X-ray sensor (NO in step S124), the process proceeds to step S128.

In step S128, the X-ray focal position calculating part 82 calculates the information (X-ray focal position, sensor irradiation angle, sensor imaging angle) on each X-ray sensor with respect to the sensor base reference angle. Specifically, the following calculation is performed.

The X-ray focal position calculating part 82 calculates the X-ray focal position corresponding to each X-ray sensor. For instance, the intersection of the line connecting the center of the X-ray sensor and the center of the examination area and the target surface is set as the X-ray focal position.

The X-ray focal position calculating part 82 calculates the sensor irradiation angle based on the X-ray focal position.

The X-ray focal position calculating part 82 calculates the sensor imaging angle β based on the X-ray focal position. The sensor imaging angle β is the angle formed by the line connecting the work 130 and the center of the X-ray sensor 23, and the X-ray sensor 23.

The X-ray focal position information is calculated in the above manner. In the present embodiment, the sensor inclination angle α and the sensor arrangement angle γ do not need to be recalculated for every X-ray focal position as they are set in advance.

Subsequently, in step S130, the X-ray focal position calculating part 82 determines whether calculation is terminated on all the sensor base reference angles.

If determined that the calculation is not terminated on all the sensor base reference angles (NO in step S130), the process returns to the process of step S128.

If determined that the calculation is terminated on all the sensor base reference angles (YES in step S130), the X-ray focal position calculating part 82 determines whether or not the X-ray focal position calculated in step S128 overlaps the X-ray focal position stored in the NG target maintenance information in the range of area coefficient D in step S131.

If determined as overlapping (YES in step S131), the X-ray focal position calculating part 82 determines whether or not a rotation limit of the reference coordinate axis is exceeded in step S134. For instance, if N X-ray sensors are arranged on the circumference of the sensor base 22, the rotation limit is about 360/N, but the rotation limit is not limited thereto, and may be expressed with other equations or may be set in advance.

If determined that the rotation limit is not exceeded (NO in step S134), the rotation angle controller 32 rotates the sensor base by a predetermined angle (sensor base maintenance angle θm) of smaller than or equal to the rotation limit in step S136 to change the position of the X-ray sensor 23, and the process returns to the process of S128. The sensor base maintenance angle θm may be set in advance or may be determined based on the sensor arrangement angle γ.

If determined that the rotation limit is exceeded (YES in step S134), the process is terminated.

If determined that the calculated X-ray focal position is not overlapping the NG target maintenance information (NO in step S131), the X-ray focal position calculating part 82 stores the calculation result on the focal position in the X-ray focal position information 92 in step S132. That is, with respect to the set examination area, the X-ray focal position, the irradiation angle θ, the sensor inclination angle α, the sensor imaging angle β, and the sensor arrangement angle γ for each X-ray sensor 23 calculated by the X-ray focal position calculating part 82 in step S128 are stored as the X-ray focal position information.

The X-ray focal position calculating part 82 performs the process (step S100 of FIG. 12) of calculating the X-ray focal position information in the above manner.

Figure 14:
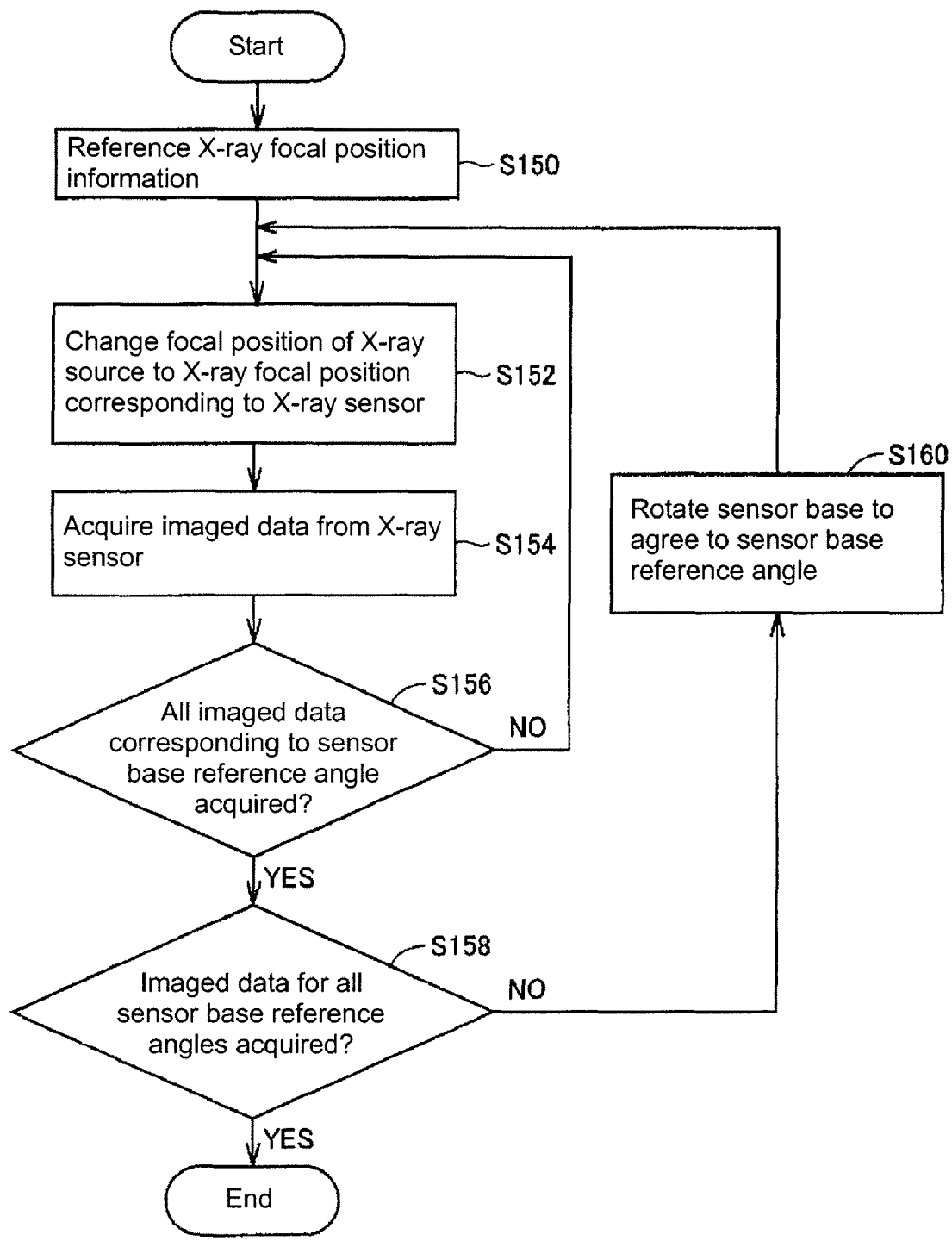
FIG. 14 shows a flowchart describing the process in step S102 of FIG. 12.

FIG. 14 shows a flowchart describing the process in step S102 of FIG. 12.

The details of the process in step S102 of FIG. 12 will be described with reference to FIG. 14. First, the scanning X-ray source controller 72 references the X-ray focal position information 92 in step S150.

In step S152, the scanning X-ray source controller 72 instructs the scanning X-ray source 10 to perform a control on the electron beam controller 62 to change the irradiating position of the electron beam to the X-ray focal position corresponding to the X-ray sensor.

Subsequently, in step S154, the image acquiring controller 74 instructs the image data acquiring part 34 to acquire imaged data from the X-ray sensor that has detected the X-ray transmitted through the examination area.

In step S156, the image acquiring controller 74 determines whether or not all the imaged data corresponding to the sensor base reference angle are acquired.

If determined that all the imaged data are not acquired (NO in step S156), the process returns to the process of step S152.

If determined that all the imaged data are acquired (YES in step S156), the image acquiring controller 76 determines whether or not the imaged data with respect to all the sensor base reference angles are acquired in step S158.

If determined that the imaged data is not acquired for all the sensor base reference angles (NO in step S158), the image acquiring controller 74 instructs the rotation angle controller 32 to perform a control to rotate the sensor base 22 so as to agree to the sensor base reference angle which has not yet been rotated to in step S160, and the process proceeds to the process of step S152.

If determined that the image data is acquired for all the sensor base reference angles (YES in step S158), the imaging process is terminated.

The imaging process (step S102 of FIG. 12) is performed in the above manner.

Figure 15:
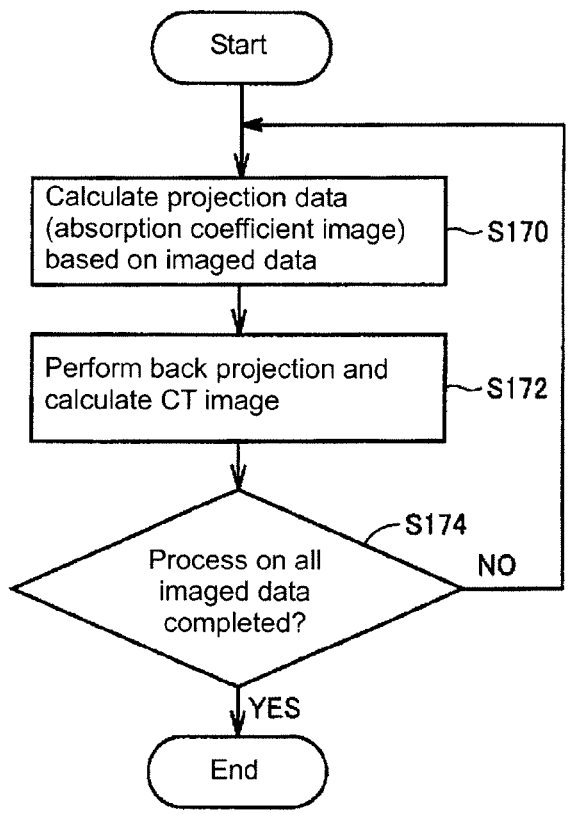
FIG. 15 shows a flowchart describing the process in step S104 of FIG. 12.

FIG. 15 shows a flowchart describing the process in step S104 of FIG. 12.

The details of the process (CT algorithm) in step S104 of FIG. 12 will be described with reference to FIG. 15.

In step S170, the 3D image reconstruction part 76 calculates projection data (absorption coefficient image) based on the acquired imaged data.

The projection data will be briefly described.

Generally, when the X-ray transmits through the examining object, the X-ray amount attenuates as expressed with the exponential function of the following equation (1) by the amount corresponding to the unique X-ray absorption coefficient of each part configuring the examining object.

$$I = I0 \mathrm{Exp}(-\mu L) \quad (1)$$

where L indicates a transmission path length, $\mu$ indicates an X-ray absorption coefficient, I0 indicates an X-ray air data value, and I indicates X-ray sensor imaged data. The X-ray air data value is imaged data of the X-ray sensor imaged without arranging the examining object, and is generally referred to as a white image.

The projection data ($\mu L$) calculated with the following equation (2) is obtained according to equation (1).

$$ML = \log(I0/I) \quad (2)$$

Various corrections are sometimes performed on the projection data or the X-ray imaged data of before calculating the projection data. For instance, a median filter may be applied to remove noise, or calibration may be performed if characteristics/sensitivity differ for every pixel in the X-ray sensor.

In step S172, the 3D image reconstruction part 76 performs reconstruction of image data based on a plurality of projection data calculated in step S170 using the data stored in the X-ray focal position information 92. Various methods such as the Fourier transformation are proposed for the reconstruction method as described in "Digital image processing" (editor: Digital image processing editorial board, published by Computer Graphics Arts Society (CG-ARTS), second edition, published March 2006), pp. 149-154. In the present embodiment, convolution back projection method is used for the reconstruction method. This is a method of back projection by convoluting the filter function such as the Shepp-Logan to the projection data to reduce blurs.

Back projection will be briefly described below.

Figure 16:
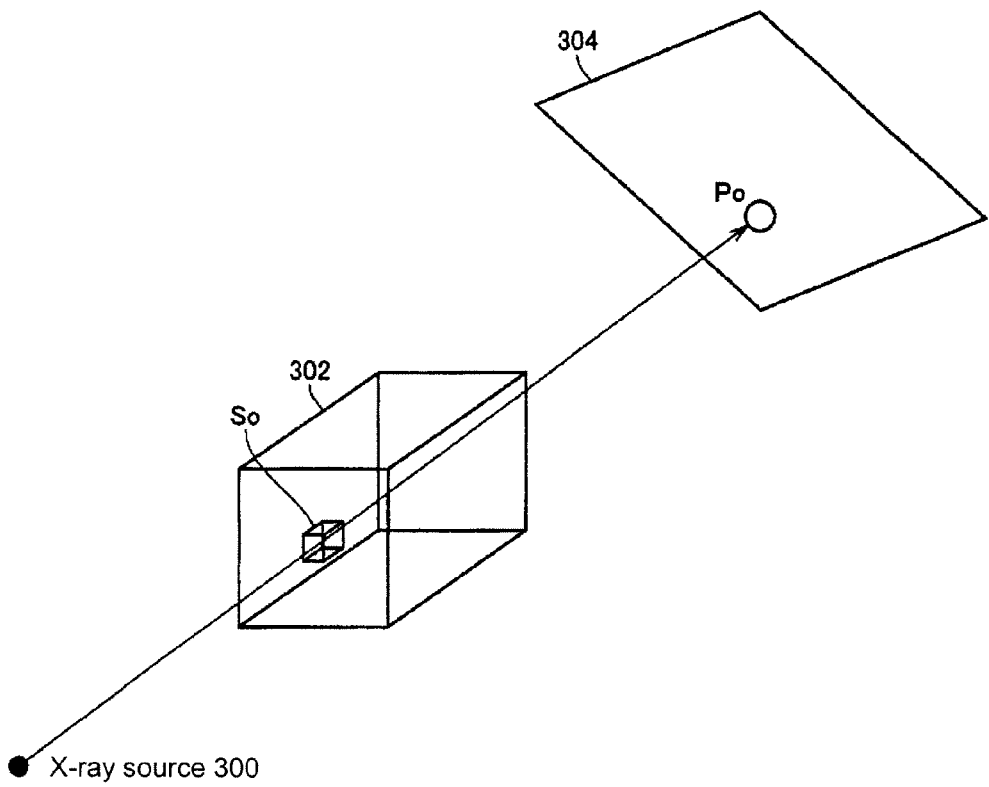
FIG. 16 shows a view describing back projection.

FIG. 16 shows a view describing back projection.

A case of back projecting voxel data S0 of the reconstruction region 302 will be described by way of example with reference to FIG. 16.

In this case, a value of the projection data of a point (pixel of X-ray sensor 304) P0 where the line connecting an X-ray source 300 and the voxel data S0 and an X-ray sensor 304 intersect is set as a value of the voxel data S0. Since the X-ray intensity differs depending on the position (coordinate) of the voxel in this case, intensity correction such as the FDK method may be performed based on the sensor inclination angle, the sensor imaging angle, the irradiation angle, the sensor arrangement angle, and the sensor base reference angle. A pixel P0 can be geometrically calculated from the information stored in the X-ray focal position information 92, and the values of the distance Z1 from the target surface to the examining target and the distance Z2 from the examining target to the center of the X-ray sensor, as shown in FIG. 5 when obtaining the pixel P0.

Returning back to FIG. 15, the 3D image reconstruction part 76 lastly determines whether or not the process on all the imaged data is completed in step S174.

If determined that the process on all the imaged data is not completed (NO in step S174), the process returns to the process of step S170.

If determined that the process on all the imaged data is completed (YES in step S174), the process is terminated.

Figure 17:
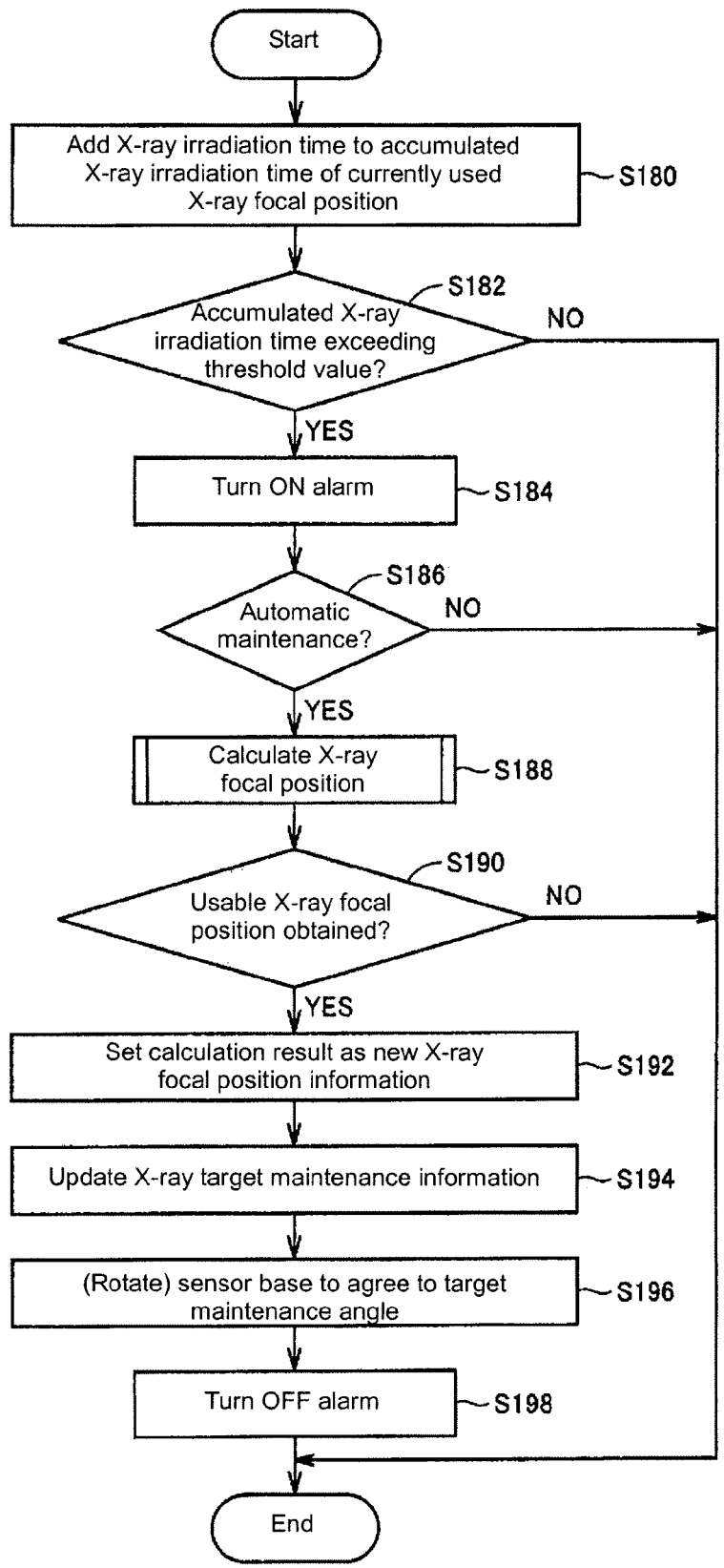
FIG. 17 shows a flowchart describing the process in step S112 of FIG. 12.

FIG. 17 shows a flowchart for describing the process in step S112 of FIG. 12.

The details of the process (lifetime judgment) in step S112 of FIG. 12 will be described with reference to FIG. 17.

In step S180, the maintenance information managing part 86 adds the irradiation time of the electron beam to the accumulated X-ray irradiation time corresponded to the X-ray focal position currently used in imaging. In imaging, the exposure time of the X-ray sensor or the X-ray irradiation time is set, and thus the maintenance information managing part 86 calculates the accumulated X-ray irradiation time based on such a setting, and updates the currently used target maintenance information. The accumulated X-ray irradiation time may be calculated based on the time set as above, but the accumulated time may be measured by counting the actual irradiation time.

In step S182, the maintenance information managing part 86 determines whether or not the accumulated X-ray irradiation time of the currently used X-ray focal position has exceeded the threshold value indicating the target lifetime.

If determined that the threshold value is not exceeded (NO in step S182), the lifetime judgment process is terminated.

If determined that the threshold value is exceeded (YES in step S182), the maintenance information managing part 86 instructs the output unit 50 to make a notification that the accumulated X-ray irradiation time exceeds the predetermined threshold value in step S184. The notification is made known to the user by turning ON the alarm, lighting a display lamp, displaying on the display, or the like.

Subsequently, in step S186, the maintenance information managing part 86 determines whether or not the maintenance of the target is automatic. Automatic maintenance is a mode of automatically changing the focal position of the X-ray and the sensor base position to enable continuous operation of the X-ray examination apparatus. Manual maintenance is a mode in which the process performed in the automatic maintenance is performed by the user while checking. The X-ray examination cannot be performed in manual maintenance. The user can perform the setting on the automatic maintenance in advance through the input unit 40.

If determined that the maintenance is not the automatic maintenance (NO in step S186), the maintenance information managing part 86 terminates the process. In this case, each process of steps S188 to 198 is performed by the user while checking. That is, the user himself/herself does not need to perform each process itself, and merely needs to proceed the process while checking the result of each step executed in the calculation unit 70.

If determined that the maintenance is the automatic maintenance (YES in step S186), the X-ray focal position calculating part 86 calculates the X-ray focal position. The details thereof will be hereinafter described.

In step S190, the maintenance information managing part 86 determines whether or not the usable X-ray focal position is obtained in step S188.

If determined that the usable X-ray focal position is not calculated in step S188 (NO in step S190), the target needs to be replaced, and the maintenance information managing part 86 terminates the lifetime judgment process.

If determined that the usable X-ray focal position is calculated (YES in step S190), the X-ray focal position calculating part 86 stores the calculation result in the X-ray focal position information 92 in step S192. The electron beam controller 62 reads the X-ray focal position information 92 and changes the X-ray focal position.

In step S194, the maintenance information managing part 86 writes the information on the target used in the previously used target maintenance information, and writes the X-ray focal position information 92 in the currently used target maintenance information, and updates the X-ray target maintenance information 91.

Subsequently, in step S196, the rotation angle controller 32 rotates the sensor base 22 so as to become the target maintenance angle calculated in step S188. In imaging, the sensor base after rotation thereafter becomes the reference (reference coordinate axis).

Finally, in step S198, the maintenance information managing part 86 turns OFF the alarm and terminates the process.

Figure 18:
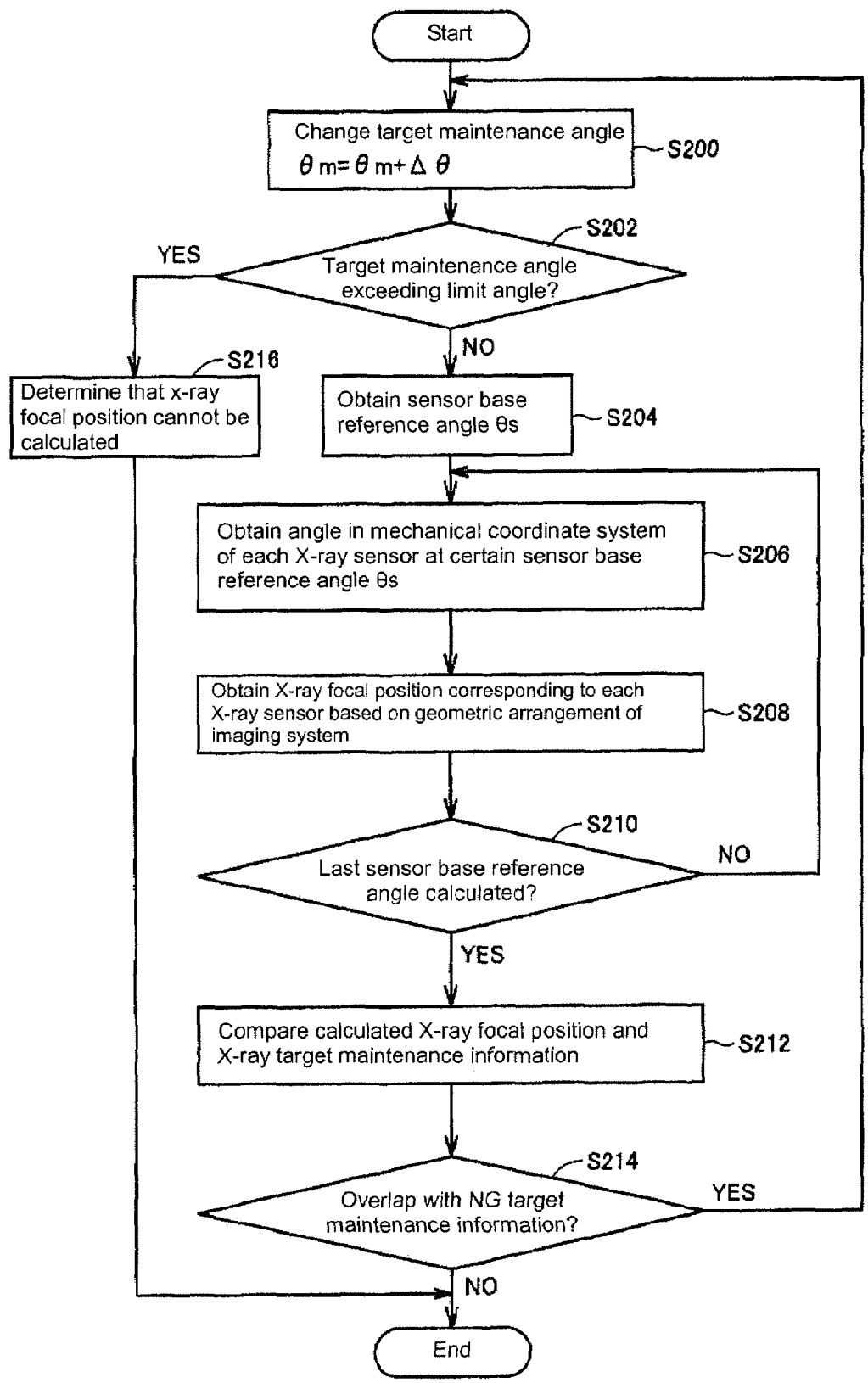
FIG. 18 shows a flowchart describing the process in step S188 of FIG. 17.

FIG. 18 shows a flowchart describing the process in step S188 of FIG. 17.

The details of the process in step S188 of FIG. 17 will be described with reference to FIG. 18. In step S200, first the X-ray focal position calculating part 82 adds a predetermined angle ($\Delta\theta$) set in advance to the target maintenance angle $\theta$m and updates the same. The calculation of the target maintenance angle is merely performed here, and the sensor base 22 is not actually rotated.

In step S202, the X-ray focal position calculating part 82 determines whether or not the target maintenance angle has exceeded a limit angle. For instance, if N X-ray sensors are arranged on the circumference of the sensor base 22, the limit angle of the target maintenance angle is about 360/N, but the limit angle is not limited thereto, and may be expressed with other equations or may be set in advance.

If determined that the target maintenance angle exceeded the limit angle (YES in step S202), the X-ray focal position calculating part 82 determines that the usable X-ray focal position cannot be calculated in step S216, and terminates the process.

If determined that the target maintenance angle has not exceeded the limit angle (NO in step S202), the X-ray focal position calculating part 82 obtains the sensor base reference angle $\theta$s in step S204. As described in steps S124, 126 in FIG. 13, determination is made on whether the set number of imaging is greater than the number of X-ray sensors attached to the circumference of the sensor base, and the sensor base reference angle is calculated if determined that the number of imaging is greater than the number of X-ray sensors. The calculation method will be omitted since the description will be redundant.

Subsequently, in step S206, the X-ray focal position calculating part 82 obtains an angle in the mechanical coordinate system of each X-ray sensor 23 in a certain sensor base reference angle $\theta$s. The sensor base 22 is rotated by the target maintenance angle $\theta$m with respect to the mechanical coordinate system indicating the absolute coordinate, and a number of sensor base reference angles $\theta$s exist with the rotated place as the reference. Therefore, the sensor base reference angle in the mechanical coordinate system becomes ($\theta$m+$\theta$s). That is, the position of each X-ray sensor 23 in the mechanical coordinate system becomes ($\theta$m+$\theta$s+$\gamma$) obtained by adding the sensor arrangement angle $\gamma$ of each X-ray sensor 23 to the ($\theta$m+$\theta$s).

In step S208, the X-ray focal position calculating part 82 obtains the X-ray focal position with respect to each X-ray sensor 23 by geometric arrangement of the imaging system based on the angle of each X-ray sensor 23 in the mechanical coordinate system obtained in step S206.

In step S210, the X-ray focal position calculating part 82 determines whether the X-ray focal position with respect to each X-ray sensor 23 is calculated for the last sensor base reference angle. If a plurality of sensor base reference angles $\theta$s is calculated in step S204, the X-ray focal position is sequentially calculated for each sensor base reference angle, and determination is made on whether the X-ray focal position is calculated for the last sensor base reference angle.

If determined that the last sensor base reference angle is not calculated (NO in step S210), the process after step S206 is performed for the next sensor base reference angle.

If determined that the last sensor base reference angle is calculated (YES in step S210), the X-ray focal position calculating part 82 compares the calculated X-ray focal position and the X-ray target maintenance information 91 in step S212. Here, comparison is performed on whether the X-ray focal position indicated by the NG maintenance information contained in the X-ray target maintenance information 91 and the calculated X-ray focal position overlap in the range having the area coefficient D as diameter or diagonal line.

In step S214, the X-ray focal position calculating part 82 determines whether overlapping the X-ray focal position of the NG target as a result of comparison in step S212.

If determined as overlapping (YES in step S214), the process returns to the process of step S200 to newly recalculate the X-ray focal position.

If determined as not overlapping (NO in step S214), the process is terminated.

According to the X-ray examination method using the X-ray examination apparatus applied with the X-ray examination device and the X-ray photographing method of the X-ray examination apparatus according to the present invention, the irradiation time at the X-ray focal position of the target surface irradiated with the electron beam is stored. If determined that a predetermined time has elapsed, the position of the X-ray sensor is changed, and the X-ray focal position on the target is moved. The user thus can manage the maintenance of the X-ray examination apparatus with a computer etc. without touching the X-ray source. Therefore, the examination can be continued without requiring time for maintenance.

Since the maintenance of the target of the X-ray source can be automatically performed, the X-ray examination apparatus can be easily and conveniently used.

Since the irradiation time on one X-ray focal position is reduced by moving the electron beam, the time until the maintenance of the target becomes longer. The frequency of carrying out the maintenance on the target is thereby reduced.

The embodiment disclosed herein is merely illustrative in all aspects, and should not be construed as being exclusive. The scope of the invention is defined by the Claims and not by the description given above, and the meaning equivalent to the Claims and all modifications within the scope of the Claims are intended to be encompassed.

What is claimed is:

1. An X-ray examination method using an X-ray examination apparatus for examining an examining portion of an object by X-ray irradiation, the apparatus including a detection surface for detecting an intensity distribution of an X-ray set and entered to a position specified out of predetermined positions, an X-ray source capable of moving an X-ray focal position on a target surface and generating the X-ray, and a storage device for storing history information on generation of the X-ray at the position on the target surface as the X-ray focal position, the method comprising the steps of:

setting the X-ray focal position corresponding to a position of the detection surface specified out of a plurality of first predetermined positions and the examining portion;

detecting that an X-ray radiation dosage generated from the set X-ray focal position has exceeded a predetermined amount based on the history information of the storage device;

changing and setting a specified position of the detection surface to one of a plurality of second predetermined positions different from the plurality of first predetermined positions according to the detection result;

moving the X-ray focal position to a position reset according to the changed detection surface, and generating the X-ray; and detecting an intensity distribution of the X-ray transmitted through the examining portion on the detection surface.

2. An X-ray examination method according to claim 1, wherein the step of setting the X-ray focal position includes a step of determining the X-ray focal position on the target surface so that the X-ray transmits through the examining portion and enters the detection surface.

3. An X-ray examination method according to claim 1, wherein the step of changing and setting the specified position includes a step of specifying a plurality of detection surfaces for detecting the X-ray out of the plurality of second predetermined positions;

the step of generating the X-ray includes steps of:

determining each of the plurality of X-ray focal positions on the target surface so that the X-ray transmits through the examining portion and enters the plurality of detection surfaces, and moving an irradiating position applied with an electron beam of the X-ray source to the each determined X-ray focal position, and generating the X-ray; and the method further comprises a step of:

reconstructing image data of the examining portion based on data of the detected intensity distribution.

4. An X-ray examination method according to claim 3, wherein the step of detecting that the X-ray radiation dosage has exceeded the predetermined amount includes a step of detecting that at least an accumulated time in which the X-ray is generated from the set X-ray focal position has elapsed a predetermined time.

5. An X-ray examination method according to claim 4, wherein the step of determining each of the plurality of X-ray focal positions includes a step of determining the X-ray focal position excluding a position applied with the electron beam beyond the predetermined time.

6. An X-ray examination method according to claim 4, wherein the step of determining each of the plurality of X-ray focal positions includes a step of determining the X-ray focal position out of a position applied with the electron beam beyond the predetermined time excluding a range determined based on an area coefficient corresponding to a size of an X-ray focus.

7. An X-ray examination method according to claim 1, wherein the step of generating the X-ray includes a step of changing an irradiation position applied with an electron beam on the target surface by deflecting the electron beam, and moving the X-ray focal position.

8. An X-ray examination apparatus for examining an examining portion of an object with X-ray, the X-ray examination apparatus comprising:

an X-ray detector having a plurality of detection surfaces for detecting the X-ray, the X-ray detector including a detection position changing part for changing the positions of the plurality of detection surfaces from a plurality of first predetermined positions to a plurality of second predetermined positions different from the plurality of first predetermined positions;

an output controller for controlling an output process of the X-ray, the output controller including:

a starting point setting part for setting, on the plurality of detection surfaces, each starting point of X-ray emission so that the X-ray transmits through the examining portion of the object and enters the each detection surface, a storage part for storing the each starting position and history information on emission of the X-ray from the each starting position in correspondence to each other, and a detection part for detecting that an accumulated irradiation time has elapsed a predetermined time on the set starting point position based on the history information in the storage part, and outputting the detection result to allow the detection position changing part to change, the starting point setting part resets the each starting point position when change is made by the detection position changing part, the apparatus further comprising:

an X-ray output part for moving an X-ray focal position of an X-ray source to the each starting position and generating the X-ray; and a reconstruction part for reconstructing image data of the examining portion based on data of an intensity distribution of the X-ray transmitted through the examining portion detected on the plurality of detection surfaces.

9. An X-ray examination apparatus according to claim 8, wherein the X-ray output part includes a part for deflecting an electron beam and moving an irradiation position on the target surface to move the X-ray focal position.

10. An X-ray examination apparatus according to claim 8, wherein the detection position changing part includes:

a rotatable base arranged with the plurality of detection surfaces on a circumference having a predetermined axis as a center; and a rotating part for rotating the rotatable base with the axis as the center;

wherein the positions of the plurality of detection surfaces are changed from the plurality of first predetermined positions to the plurality of second predetermined positions by rotating the rotatable base by a constant angle according to the detection result of the detection part.

11. An X-ray examination apparatus according to claim 8, wherein the starting point setting part sets the each starting point position excluding the position associated with an irradiation time that has elapsed the predetermined time based on the history information.

12. An X-ray examination apparatus according to claim 8, wherein the output part further includes a specifying part for specifying an examining portion of the object.

* * * * *